(12) United States Patent
Maeda et al.

(10) Patent No.: US 9,574,512 B2
(45) Date of Patent: Feb. 21, 2017

(54) APPARATUS FOR DETECTING PARTICULATE MATTER AND CORRECTION METHOD OF APPARATUS FOR DETECTING PARTICULATE MATTER

(75) Inventors: Eriko Maeda, Okazaki (JP); Takehito Kimata, Kariya (JP)

(73) Assignee: DENSO CORPORATION, Kariya (JP)

( * ) Notice: Subject to any disclaimer, the term of this patent is extended or adjusted under 35 U.S.C. 154(b) by 628 days.

(21) Appl. No.: 13/451,706

(22) Filed: Apr. 20, 2012

(65) Prior Publication Data

US 2012/0266646 A1    Oct. 25, 2012

(30) Foreign Application Priority Data

Apr. 21, 2011 (JP) ................. 2011-094654
Jan. 10, 2012 (JP) ................. 2012-001803

(51) Int. Cl.
| | |
|---|---|
| *F02D 41/14* | (2006.01) |
| *F02D 41/24* | (2006.01) |
| *G01N 15/06* | (2006.01) |
| *G01N 35/00* | (2006.01) |

(52) U.S. Cl.
CPC ....... *F02D 41/1466* (2013.01); *F02D 41/2432* (2013.01); *F02D 41/2474* (2013.01); *G01N 15/0656* (2013.01); *G01N 35/00693* (2013.01)

(58) Field of Classification Search
None
See application file for complete search history.

(56) References Cited

U.S. PATENT DOCUMENTS

| | | |
|---|---|---|
| 2009/0051376 A1 | 2/2009 | Schnell et al. |
| 2010/0000863 A1 | 1/2010 | Kondo et al. |
| 2010/0051458 A1 | 3/2010 | Teranishi et al. |
| 2010/0206167 A1 | 8/2010 | Okayama et al. |

FOREIGN PATENT DOCUMENTS

| | | |
|---|---|---|
| JP | 59-197847 | 11/1984 |
| JP | 2008-502892 | 1/2008 |
| JP | 2009-097868 | 5/2009 |
| JP | 2010-032488 | 2/2010 |
| JP | 2010-054432 | 3/2010 |
| JP | 2010-190615 | 9/2010 |
| JP | 2011-080942 | 4/2011 |

OTHER PUBLICATIONS

Office Action (3 pages) dated Aug. 6, 2013, issued in corresponding Japanese Application No. 2012-001803 and English translation (3 pages).

*Primary Examiner* — Robert R Raevis
(74) *Attorney, Agent, or Firm* — Nixon & Vanderhye P.C.

(57) ABSTRACT

An apparatus for detecting particulate and a correction method of the apparatus for detecting particulate matter that detects particulate matter within a gas to be measured are provided. The correction method corrects the individual differences inevitably occurring during the manufacturing process of particulate matter detection sensors. The apparatus for detecting particulate matter includes an applied voltage correction means. The applied voltage correction means applies correction information acquired by the correction method to detection control.

12 Claims, 17 Drawing Sheets

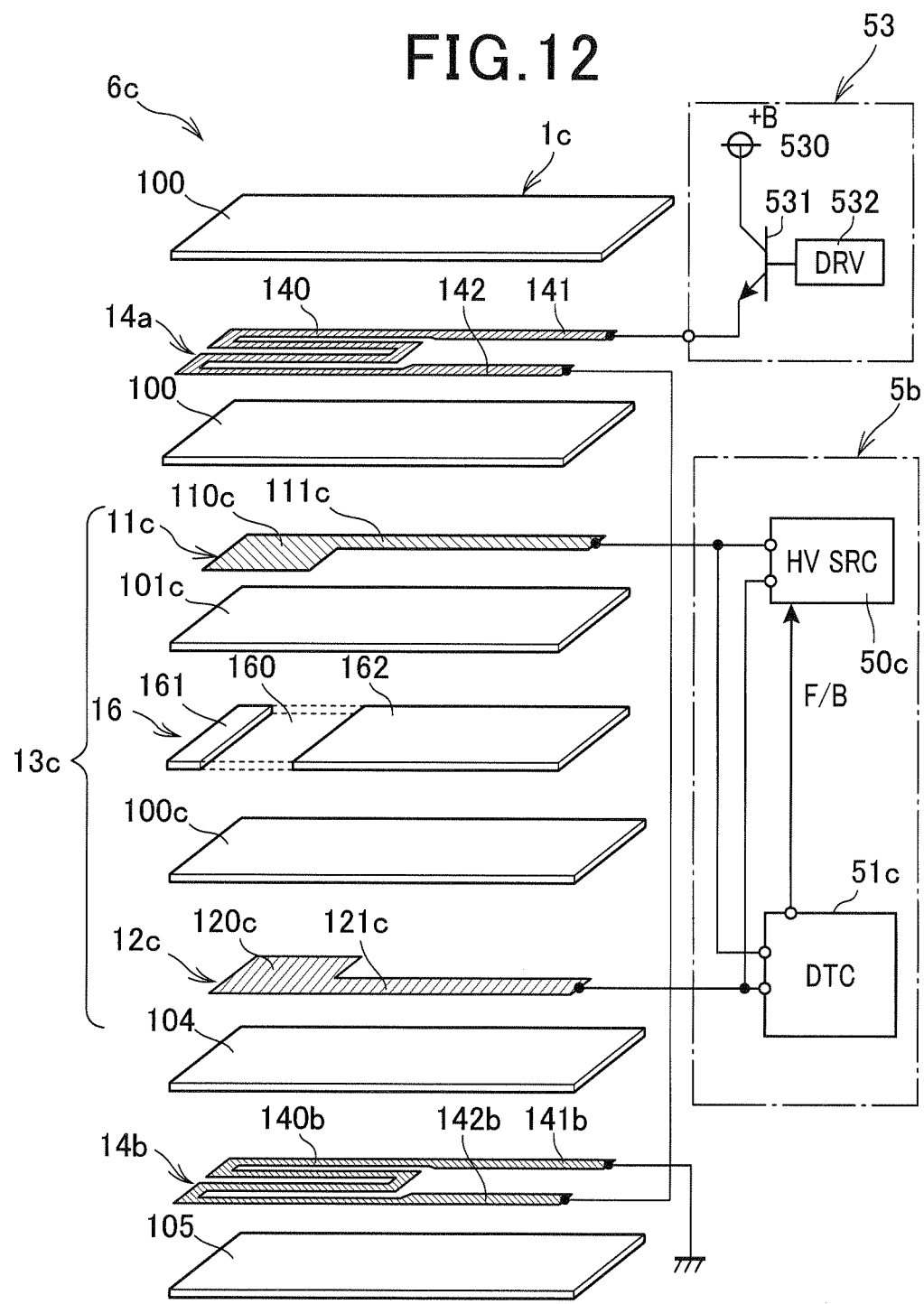

APPARATUS FOR DETECTING PARTICULATE MATTER AND CORRECTION METHOD OF APPARATUS FOR DETECTING PARTICULATE MATTER

CROSS REFERENCE TO RELATED APPLICATION

This application is based upon and claims the benefit of priority from the prior Japanese Patent Application No. 2011-94654, filed Apr. 21, 2011, and the prior Japanese Patent Application No. 2012-1803, filed Jan. 10, 2012, the entire content of which is incorporated herein by reference.

BACKGROUND OF THE INVENTION

1. Field of the Invention

The present invention relates to an apparatus for detecting particulate matter and a correction method of apparatus for detecting particulate matter that is, for example, used in an exhaust gas purification system of a vehicle internal combustion engine. The apparatus for detecting particulate matter detects the particulate matter present in measured gas.

2. Description of the Related Art

In a diesel engine of an automobile and the like, a diesel particulate filter (hereinafter referred to accordingly as "DPF") is provided on an exhaust gas path. The DPF collects environmental pollutants included in exhaust gas, particularly particulate matter (PM) mainly composed of soot particles and soluble organic fractions (SOF). The DPF is made of a porous ceramic having excellent heat resistance. The DPF captures the PM as a result of the exhaust gas passing through a partition wall having numerous fine pores.

When the amount of collected PM exceeds an allowable amount, the DPF becomes clogged. Negative pressure may increase. Alternatively, the amount of PM escaping through the DPF may increase. Therefore, collection capability is required to be recovered by a regeneration process of the DPF being periodically performed.

In general, the regeneration timing of the DPF is determined by the detection of increase in differential pressure at both ends of the DPF caused by increase in the amount of collected PM. Therefore, a differential pressure sensor is provided that detects the difference in pressure upstream and downstream from the DPF.

The DPF is regenerated by high-temperature exhaust gas being introduced into the DPF through heating using a heater or by post-injection, and the PM being removed by burning.

On the other hand, a PM detection sensor is also proposed that directly detects the PM in the exhaust gas, for example, in JP-A-S59-197847 and JP-A-2008-502892. The PM detection sensor is, for example, provided downstream from the DPF and measures the amount of PM escaping through the DPF. Therefore, the PM detection sensor can be used in an on-board diagnosis (OBD) device to monitor an operating state of the DPF or to detect abnormalities (such as cracks and damage).

Furthermore, use of the PM detection sensor in place of the differential pressure sensor to determine the regeneration timing of the DPF is also being discussed. In this instance, the PM detection sensor is provided upstream from the DPF and measures the amount of PM entering the DPF.

JP-A-S59-197847 discloses an electrical-resistance-type smoke sensor. The smoke sensor is configured such that a pair of comb-shape electrodes is formed on a front surface of a substrate having insulating properties, and a heating element is formed on a back surface of or within the substrate. This type of smoke sensor takes advantage of smoke (particulate carbon) having conductivity, and detects electrical resistance generated when smoke accumulates between the electrodes that serve as a detecting section. Heat-resistant insulating material is used as substrate material. Noble metal such as platinum, silver or the like is used as electrode material. A pair of electrodes is formed by screen-printing noble metal paste on a front surface of a plate-shaped substrate.

On a back surface of the substrate, a heating element is formed at the opposite of the electrode. The detecting section is heated to a desired temperature such as from 400° C. to 1000° C., thereby burning away the deposited smoke. Then, inter-electrode resistance is measured. As a result, detection capability of the sensor is restored.

JP-A-2008-502892 discloses a method for controlling deposition of soot on a sensor. In this method, a high voltage is applied between sensing electrodes. An electric field is generated between the electrodes. The PM passing near the sensing electrodes is attracted by electrostatic attractive force generated by the electric field. Collection of PM is promoted. The collected PM is accumulated between the sensing electrodes. As a result of measurement of the electrical resistance between the sensing electrodes that changes depending on the amount of accumulated PM, the amount of accumulated PM is measured.

The electrical characteristics used to detect the PM within a gas to be measured is not limited to the electrical resistance that changes depending on the amount of PM accumulated between the sensing electrodes. Various electrical characteristics, such as capacitance or changes in current accompanying electrochemical reaction, can also be used.

JP-A-2010-32488 discloses an apparatus for detecting particulate matter that uses resistance, inductance, capacitance, and impedance as the electrical characteristics. The apparatus for detecting particulate matter includes a plate-shaped first electrode, a second electrode, a power supply for dust collection, a pair of measuring electrodes, a characteristic measuring means, and a means for calculating amount of particulate matter. One surface of the first electrode is covered by a dielectric (referred to as an inter-electrode dielectric). The second electrode forms a pair with the first electrode. The power supply for dust collection applies voltage. The pair of measuring electrodes is disposed on the surface of the inter-electrode dielectric such as to oppose each other. The second electrode is disposed on the side of the one surface of the first electrode with a space therebetween. A gas containing PM flows through this space. Electricity is discharged as a result of voltage applied between the first electrode and the second electrode. The characteristic measuring means measures the electrical characteristics between the pair of measuring electrodes. The means for calculating amount of particulate matter determines the amount of PM collected on the surface of the inter-electrode dielectric, based on the amount of change in electrical characteristics measured by the characteristic measuring means.

On the other hand, JP-A-2010-54432 discloses a sensor detecting an amount of carbon. The amount of carbon detection sensor includes at least a proton conductor, an electrode pair, and a power supply. The proton conductor is composed of a solid electrolyte having proton conductivity. The electrode pair is composed of a measuring electrode and a reference electrode formed on the surface of the proton conductor. The power supply applies a predetermined current or voltage between the electrode pair. The measuring electrode is disposed on the opposite side of the gas to be measured and the reference electrode is isolated from the gas to be measured. As a result of measurement of the changes in current or voltage flowing by electrochemical reaction with the PM within the gas to be measured on the surface of the measuring electrode, the amount of PM is detected.

In general, sensors, such as PM detection sensors and oxygen detection sensors, are fixed to a flow path of the gas to be measured, via a housing. For example, in JP-A-2009-97868, a detecting element placed within the gas to be measured is protected by being covered by a substantially cylindrical cover body having a predetermined hole.

However, in an actual manufacturing process, it is difficult to match the direction of the detecting element of the sensor element with the direction of the inlet for gas to be measured provided in each cover body when assembling the sensor element and the cover body to the housing, for each sensor. When the direction of the sensor element is matched with the direction of the cover body for each sensor, work efficiency becomes extremely poor. Manufacturing costs of the particulate matter detection sensor increases.

On the other hand, when the particulate matter detection sensor is assembled with no regard for the direction of the sensor element and the direction of the cover body, work efficiency improves. However, the direction of the detecting element and the direction of the inlet for gas to be measured provided in the cover body vary. The flow of gas to be measured that is introduced into the cover body differs with each sensor. As a result, individual differences in output in relation to the collecting performance of particulate matter contained within the gas to be measured in the detecting element and the amount of accumulated particulate matter become greater. Reliability as a sensor significantly decreases.

In some instances, a plurality of electrodes for collecting may be disposed within a single sensor element. The collection electrode collects the PM using electrostatic attractive force by applying an electric field to the PM to be detected. In addition to the collection electrodes, a sensing electrode for detecting electrical characteristics may be provided. In these instances, variations inevitably occur in the actual distance between electrodes. The variations in inter-electrode distance cause variations in field strength generated between the electrodes. The amount of PM collected in the detecting element changes, and individual differences in detection results occur.

The distance between electrodes that have been actually manufactured can be measured by image processing or the like. However, it is very difficult to reduce the variations in output results through classification of each sensor element into ranks based on the distribution of inter-electrode distance within a manufacturing lot or the like. Cost effectiveness is also poor.

Moreover, a method is also known in which the sensor element is provided with a through hole. The electrodes for collecting are set above and below the through hole. As a result of an electric field being generated between the collection electrodes, the PM is collected. However, even in this method, ensuring the distance between electrodes is difficult. Individual differences occur in the field strength that is actually generated. Variations in output results occur.

SUMMARY OF THE INVENTION

The present invention has been achieved in light of the above-described issues. An object of the present invention is to provide an apparatus for detecting particulate matter that detects the amount of particulate matter contained within a gas to be measured to detect, with high accuracy, the particulate matter contained within the gas to be measured. The apparatus for detecting particulate matter includes a correction method and a correcting means. The correction method corrects the individual differences inevitably occurring during the manufacturing process of particulate matter detection sensors. The correcting means applies correction information acquired by the correction method to detection control.

A first aspect of the invention is an apparatus for detecting particulate matter that detects particulate matter within a gas to be measured. The apparatus for detecting particulate matter includes a particulate matter detection sensor, a field generation power unit and a measuring section. The particulate matter detection sensor includes at least a sensor element that has the detecting element in which an electrode for collecting or an electrode provided separately from the electrode for collecting is used as a sensing electrode that detects an electrical characteristic that changes depending on the amount of particulate matter collected in the detecting element, the electrode for collecting being to collect the particulate matter within the gas to be measured in a detecting element using attractive force generated by an electric field generated by the field generation power unit; a cover body that protects the sensor element; and a housing that places the detecting element in the gas to be measured. The measuring section measures the electrical characteristic that changes depending on the amount of particulate matter within the gas to be measured that is collected in the detecting element. In the apparatus for detecting particulate matter, an applied voltage correction means is provided. A dead mass is a value until output is produced in relation to a gas to be measured for calibration containing a known amount of particulate matter becomes a predetermined threshold or more. When the dead mass is equal to or greater than a dead mass of a particulate matter detection sensor for calibration serving as reference, the applied voltage correction means holds the voltage applied by the field generation power unit at a predetermined applied voltage value and maintains field strength to reduce the dead mass. When the dead mass is less than the dead mass of the particulate matter detection sensor for calibration serving as reference, the applied voltage correction means sets the voltage applied by the field generation power unit to be lower than a predetermined lower threshold applied voltage or higher than a predetermined upper threshold applied voltage, and corrects the field strength to increase the dead mass.

A second aspect of the invention is a correction method of the apparatus for detecting particulate matter described above. A dead mass is a value until output is produced in relation to a gas to be measured for calibration containing a known amount of particulate matter becomes a predetermined threshold or more. In the correction method, when a dead mass is equal to or greater than a dead mass of a particulate matter detection sensor for calibration serving as reference, the voltage applied to the detecting element is held within a range from a predetermined lower threshold applied voltage to a predetermined upper threshold applied voltage at which field strength is that which minimizes the dead mass. When the dead mass is less than the dead mass of the particulate matter detection sensor for calibration serving as reference, the voltage applied between sensing electrodes by the field generation power unit is set to be lower than the predetermined lower threshold applied voltage or higher than the predetermined upper threshold applied voltage, and the dead mass is brought closer to the dead mass of the particulate matter detection sensor for calibration.

BRIEF DESCRIPTION OF THE DRAWINGS

In the accompanying drawings:
FIG. 1A is a top view of the sensor element;
FIG. 1B is a general view of the apparatus for detecting particulate matter;
FIG. 4A is a characteristics diagram showing variations of the sensor output in relation to the known amount of particulate matter;
FIG. 4B is a characteristics diagram showing the dispersion of the dead mass;
FIG. 5A is a characteristics diagram showing variations of the sensor output in relation to the known amount of particulate matter;
FIG. 5B is a characteristics diagram showing the dispersion of the dead mass;
FIG. 6A is a characteristics diagram showing variations of sensor output in relation to the known amount of particulate matter;
FIG. 6B is a characteristics diagram showing the dispersion of the dead mass;
FIG. 7A is a deployment perspective view;
FIG. 7B is a main portion cross-sectional view.

FIG. 10A is a characteristics diagram showing variations of sensor output in relation to the known amount of particulate matter;
FIG. 10B is a characteristics diagram showing the dispersion of he dead mass;
FIG. 11A and FIG. 11B are diagrams showing the effect of the apparatus as shown FIG. 8 as an example 2 of the present invention, in which
FIG. 11A is a characteristics diagram showing a relationship between the field strength and the collecting performance, the field strength being generated by the voltage applied between the sensing electrodes,
and FIG. 11B is a characteristics diagram showing a relationship between the field strength and the dead mass;
FIG. 12 is a deployment perspective view showing a modification of an apparatus for detecting particulate matter according to the second embodiment of the present invention;
FIG. 15A is a characteristics diagram showing variations of the sensor power in relation to the known amount of particulate matter;
FIG. 15B is a characteristics diagram showing the dispersion of the dead mass;
FIG. 16A is a characteristics diagram showing a relationship between the field strength and the collecting performance, the field strength being generated by the voltage applied between the sensing electrodes;
FIG. 16B is a characteristics diagram showing a relationship between the field strength and the dead mass.

DETAILED DESCRIPTION OF THE PREFERRED EMBODIMENTS

Figure 1A:
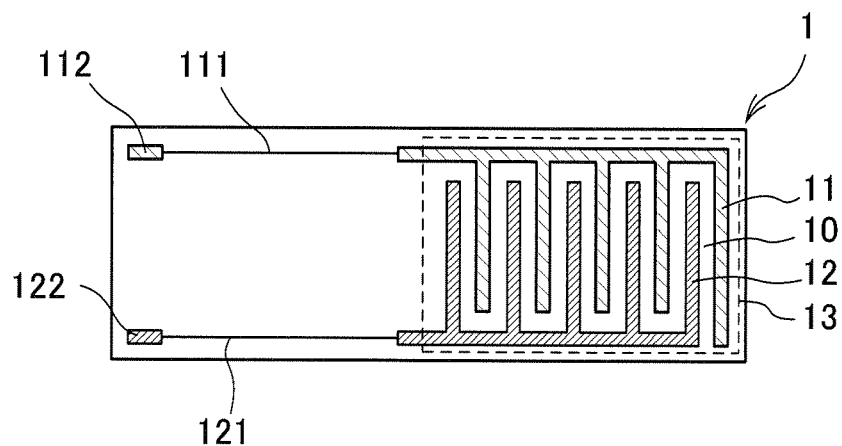
FIG. 1A and FIG. 1B are schematic diagrams showing an overview of the apparatus for detecting particulate matter according to a first embodiment of the present invention.

An apparatus for detecting particulate matter and a correction method for detecting particulate matter according to the preferred embodiments of the present invention will hereinafter be described with reference to the drawings.
First Embodiment (FIG. 1 to FIG. 6)
An apparatus for detecting particulate matter 6 according to a first embodiment of the present invention will be described with reference to FIG. 1A, FIG. 1B, and FIG. 2A to FIG. 2C. The apparatus for detecting particulate matter 6 according to the first embodiment is applied to an exhaust emission control device of an internal combustion engine and is used to detect discharged particulate matter. Specifically, the apparatus for detecting particulate matter 6 is set downstream of a diesel particulate filter (DPF) and is used to detect abnormality in the DPF. Alternatively, the apparatus for detecting particulate matter 6 is set upstream of the DPF and is used in a system that directly detects the particulate matter flowing into the DPF. Here, the apparatus for detecting particulate matter 6 detects the PM within the gas to be measured.

The apparatus for detecting particulate matter 6 according to the first embodiment includes a particulate matter detection sensor 4 and a detection control section 5.

The particulate matter detection sensor 4 is configured by a sensor element 1, a cover body 12, and a housing 3. The sensor element includes sensing electrodes 11 and 12 that detect electrical characteristics that change detecting on the amount of PM collected in a detecting element 13. The cover body 2 protects the sensor element 1. The housing 3 places the detecting element 13 in the gas to be measured.

The detection control section 5 is configured by a power unit 50 and a measuring section 51.

The power unit 50 serves as a power supply unit for measuring and a field generation power unit. The power supply unit for measuring measures electrical characteristics, such as resistance values, that change depending on the amount of PM accumulated between the sensing electrodes 11 and 12. The field generation power unit applies a high voltage between the sensing electrodes 11 and 12 of the sensor element 1, and generates an electric field between the sensing electrodes 11 and 12.

The measuring section 51 measures electrical characteristics that change depending on the amount of PM contained within the gas to be measure accumulated in the detecting element 13.

The power unit 50 and the measuring section 51 are described in detail hereafter.

Figure 2A:
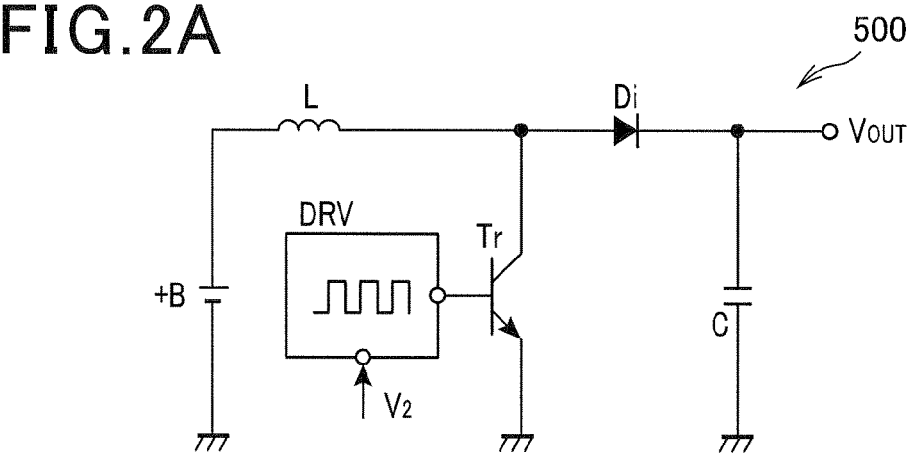
FIG. 2A is a circuit diagram showing an example of booster circuit used in the apparatus for detecting particulate matter as shown FIG. 1A.
Figure 2B:
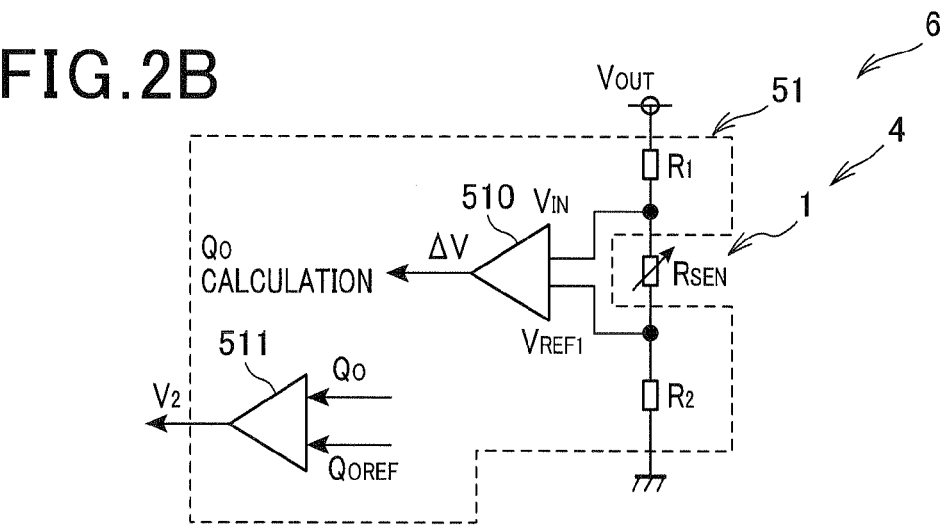
FIG. 2B is a circuit diagram showing an example of resistance detection circuit and applied voltage correction means.
Figure 2C:
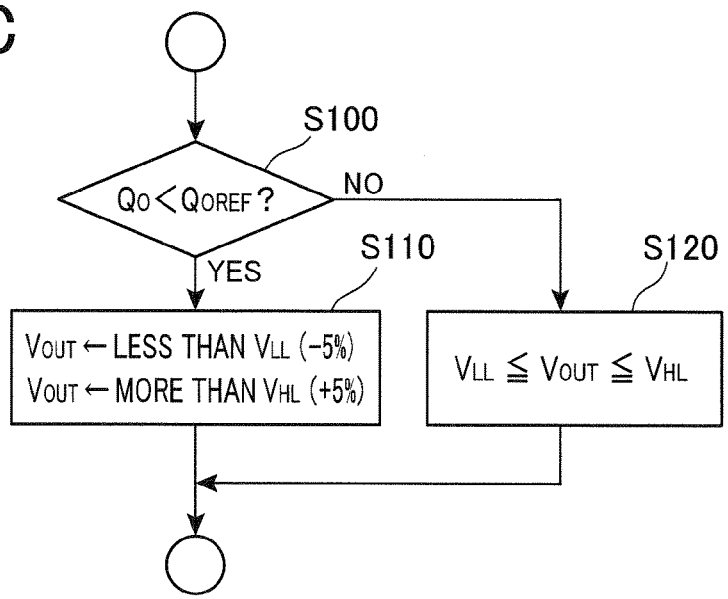
FIG. 2C is a flowchart of correction method for detecting particulate matter according to the first embodiment of the present invention.

In particular, the present invention is characteristic in that an applied voltage correction means 511 that corrects field strength is provided in adherence to the correction method described hereafter, with reference to FIG. 2A to FIG. 2C. In the applied voltage correction means 511, when a dead mass $Q_0$ is equal to or greater than dead mass $Q_{0REF}$, the voltage applied by the field generation power unit 50 is held at a predetermined applied voltage value $V_{OUT}$ ($V_{LL} \leq V_{OUT} \leq V_{HL}$) and field strength that reduces the dead mass $Q_0$ is maintained. The dead mass $Q_0$ is a value until the output is produced in relation of a gas to be measured for calibration containing a known amount of PM becomes a predetermined threshold $V_{REF}$ or higher. The dead mass $Q_{0REF}$ is a value of a particulate matter detection sensor for calibration $4_{REF}$ (referred to, hereinafter, as a sensor for calibration $4_{REF}$) serving as reference. When the dead mass $Q_0$ is less than the dead mass $Q_{0REF}$ of the sensor for calibration $4_{REF}$ serving as reference, the voltage $V_{OUT}$ applied by the field generation power unit 50 is decreased to be lower than a predetermined lower threshold applied voltage $V_{LL}$ or higher than a predetermined upper threshold applied voltage $V_{HL}$ and the field strength is corrected to increase the dead mass $Q_0$.

In addition, the dead mass $Q_{0REF}$ of the sensor for calibration $4_{REF}$ is a value measured at an applied voltage $V_{OUT}$ in which the field strength becomes 1.0 kV/mm. Using this measurement value, correction is performed in adherence to the correction method described hereafter.

As shown in FIG. 1A, the detecting element 13 of the sensor element 1 is formed by the pair of sensing electrodes 11 and 12. The sensing electrodes 11 and 12 are disposed on a surface of an insulating substrate 10 such as to oppose each other with a certain amount of space therebetween.

The sensing electrodes 11 and 12 are so-called comb-shaped electrodes, each formed into a comb shape. The sensing electrodes 11 and 12 having mutually differing polarities are disposed such as to oppose each other and are aligned in an alternating manner at a constant interval. The sensing electrodes 11 and 12 also serve as electrodes for collecting. The sensing electrodes 11 and 12 apply an electric field to the PM within the gas to be measured, using the attractive force generated by the electric field generated by the field generation power unit (power unit 50). The sensing electrodes 11 and 12 then collect the PM in the detecting element 13 using electrostatic attractive force. The electrodes for collecting also include an instance in which the PM is collected using at least attractive force, such as electrostatic force generated by the electric field generated by the field generation power unit 50, and other attractive force, such as friction force and inertia force, is simultaneously used.

The sensor element 1 is connected to sensing electrode terminal portions 112 and 122 via sensing electrode lead portions 111 and 121. The sensing electrodes 11 and 12 are connected to the detection control section 5 provided externally.

The insulating substrate 10 is composed of an insulating, heat-resistant material, such as alumina, titania, or spinel. The insulating substrate 10 is formed to be substantially plate-shaped by a known manufacturing method, such as the doctor blade method or the compression molding method.

The sensing electrodes 11 and 12 are composed of a conductive material, such as platinum, and are formed by a known manufacturing method, such as screen printing, plating, or vapor deposition.

Figure 1B:
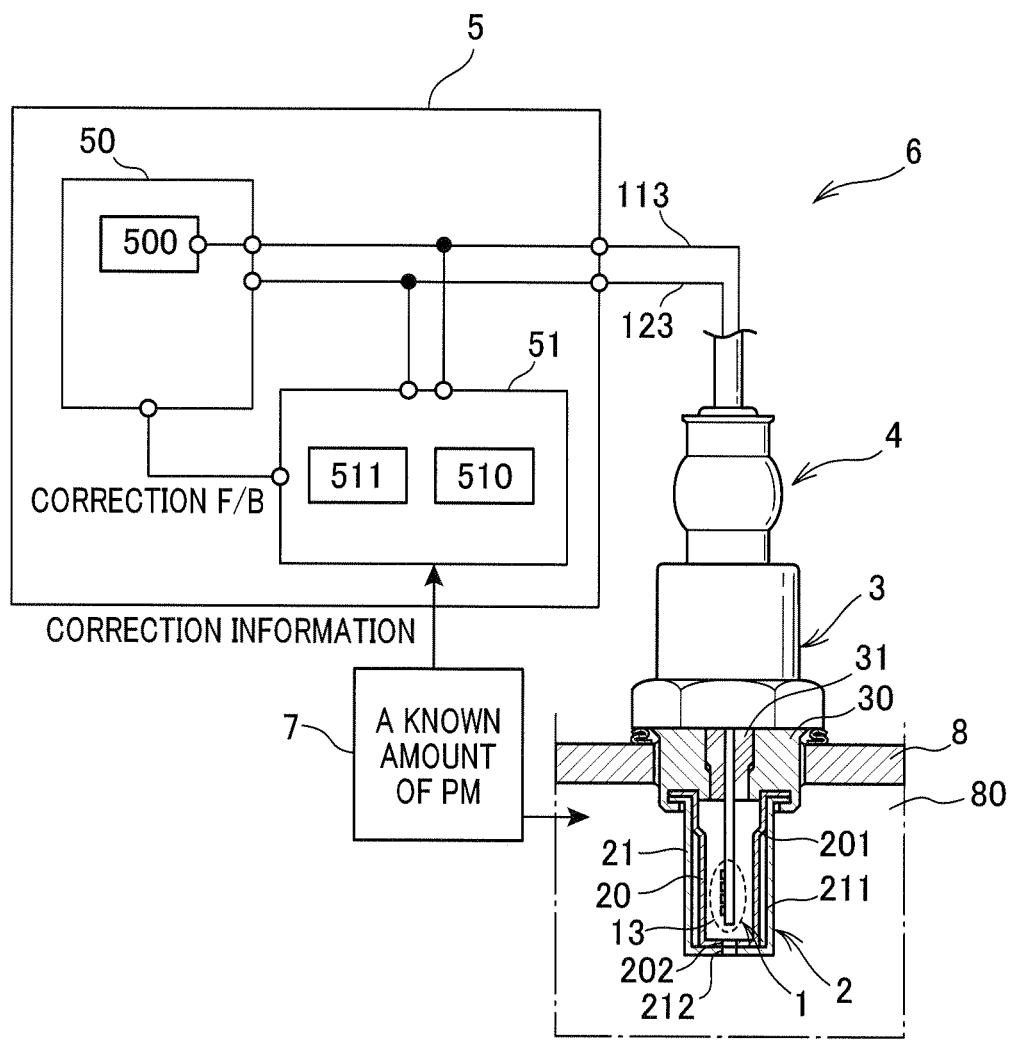

As shown in FIG. 1B, the detecting element 13 that is exposed to the gas to be measured is covered by the cover body 2. The cover body 2 is formed into a bottomed, substantially cylindrical shape. The sensor element 1 is held in an insulated manner and fixed to the interior of a housing base 30 with an insulator 31 therebetween. The housing base 30 is formed into a substantially cylindrical shape. The sensor element 1 is fixed to a flow path for gas to be measured 8, through which gas to be measured 80 flows, by the housing 3.

The cover body 2 has a double cylinder structure in which an inner cylinder 20 and an outer cylinder 21, formed into a bottomed cylindrical shape, are overlapped. The inner cylinder 20 is provided with cover holes 201 and 202. The outer cylinder 21 is provided with cover holes 211 and 212. The gas to be measured is guided to the detecting element 13 of the sensor element 1 via the cover holes 201, 202, 211, and 212 while reducing the flow rate of the gas to be measured. As a result, a flow path is configured such that the grain size of the particulate matter guided to the detecting element 13 with the gas to be measured is within a range smaller than a certain size.

The sensing electrode terminal portions 112 and 122 of the sensor element 1 are connected to the detection control section 5 by a pair of signal lines 113 and 123.

For example, as shown in FIG. 2A, the power unit 50 includes a booster circuit 500, such as a DC-DC converter, that boosts a power supply voltage+B to a predetermined voltage. According to the first embodiment, a semiconductor switching element Tr, such as an insulated gate bipolar transistor (IGBT) or a metal-oxide-semiconductor field-effect transistor (MOSFET), is opened and closed by driving signals from a drive circuit DRV. Energy stored in a choke coil L is discharged redundantly to a capacitor C. The voltage is then boosted to an output voltage $V_{OUT}$ that is higher than the power supply voltage+B and applied between the sensing electrodes 11 and 12.

At this time, the voltage applied between the sensing electrodes 11 and 12 can be increased or decreased by pulse width modulation (PWM) control or pulse frequency modulation (PFM) control by the driving signals that are oscillated from the drive circuit DRV and that opens and closes the switching element Tr. In PWM control, the output voltage $V_{OUT}$ is controlled by the duty ratio being adjusted by modulation of the pulse width, with the frequency held constant. In PFM control, the output voltage $V_{OUT}$ is controlled by modulation of the pulse frequency, with the pulse width held constant.

The configuration of the booster circuit 500 is not limited to this example.

As shown in FIG. 1B, the measuring section 51 is configured by a means for measuring sense resistance 510 and the applied voltage correction means 511.

The means for measuring sense resistance 510 measures sense resistance $R_{SEN}$ as an electrical characteristic that changes depending on the amount of particulate matter accumulated between the sensing electrodes 11 and 12.

The applied voltage correction means 511 compares the sense resistance $R_{SEN}$ measured by the means for measuring sense resistance 510 in relation to the known amount of particulate matter with a standard sense resistance $R_{REF}$ that is standard in relation to the known amount of particulate matter. The applied voltage correction means 511 then determines a correction method based on the amount of deviation from the standard sense resistance $R_{REF}$.

More specifically, as shown in FIG. 2B, the means for measuring sense resistance 510 is configured by, for example, resistor dividers $R_1$ and $R_2$ and a differential amplifier circuit element. The resistor dividers $R_1$ and $R_2$ are disposed in series in relation to the sense resistor $R_{SEN}$. The differential amplifier circuit element measures a potential difference $\Delta V$ of both ends of the sense resistor $R_{SEN}$.

The applied voltage $V_{OUT}$ is prorated by the resistor dividers $R_1$ and $R_2$ and the sense resistor $R_{SEN}$. As a result of the potential difference $\Delta V = V_{IN} - V_{REF1}$ of both ends of the sense resistor $R_{SEN}$ being measured by the differential amplifier circuit element or the like, the sense resistance $R_{SEN}$ can be identified.

The change in sense resistance $R_{SEN}$ in relation to a gas to be measured for calibration containing carbon particulates simulating the known amount of particulate matter can be measured in advance. When the gas to be measured containing an unknown amount of particulate matter is detected, the amount of particulate matter accumulated between the sensing electrodes 11 and 12 can be calculated from the relationship between the sense resistance $R_{SEN}$ and the amount of particulate matter.

In the particulate matter detection sensor 4 according to the first embodiment, the space between the sensing electrodes 11 and 12 is in an insulated state unless particulate matter is accumulated between the sensing electrodes 11 and 12. The electrical resistance between the sensing electrodes 11 and 12 is extremely large. A dead period during which detection of sensor output is difficult is present until a certain amount of particulate matter accumulates between the sensing electrodes 11 and 12.

The amount of particulate matter accumulated until the certain amount of particulate matter or more is accumulated between the sensing electrodes 11 and 12, the sensor output exceeds the predetermined threshold $V_{REF}$, and output can be detected is the dead mass $Q_0$.

The applied voltage correction means 511 compares the dead mass $Q_0$ with the dead mass $Q_{0REF}$ of the sensor for calibration 4REF. The dead mass $Q_0$ is that at which the sense resistance RSEN detected by the means for measuring sense resistance 510 using the gas to be measured for calibration containing the known amount of particulate matter is a predetermined threshold or greater than this threshold. The dead mass $Q_{0REF}$ is detected by an external correction means 7 in relation to the gas to be measured for calibration. The applied voltage correction means 511 then increases and decreases the voltage applied by the power unit 50 (referred to, hereinafter, as applied voltage VOUT) such that the dead mass $Q_0$ and the dead mass $Q_{0REF}$ match.

For example, as shown in FIG. 2C, in a dead mass judging procedure at Step 5100, the dead mass $Q_0$ in relation to the known amount of particulate matter is compared with the dead mass $Q_{0REF}$ of the sensor for calibration $4_{REF}$. When the dead mass $Q_0$ of the particulate matter detection sensor 4 to be corrected is less than the dead mass $Q_{0REF}$ of the sensor for calibration $4_{REF}$ (i.e., YES in Step S100), the operation proceeds to an applied voltage increasing/decreasing procedure at Step 5110. The applied voltage VouT is set to be lower than the lower threshold applied voltage VLL (such as about −5%) or higher than the upper threshold applied voltage $V_{HL}$(such as about +5%), such as to be outside the range of a predetermined reference voltage. As a result, the output result can be brought closer to the output result of the sensor for calibration 4.

On the other hand, at Step 5100, when the dead mass $Q_0$ of the particulate matter detection sensor 4 equal to or to be corrected is greater than the dead mass $Q_{0REF}$ of the sensor for calibration $4_{REF}$ (i.e., NO in Step S100), the operation proceeds to an applied voltage maintaining procedure at Step S 120. The applied voltage $V_{OUT}$ is maintained within a range that is the lower threshold applied voltage $V_{LL}$ or higher and the upper threshold applied voltage $V_{HL}$or lower. As a result, the applied voltage $V_{OUT}$ can be maintained so as not to deviate significantly from the output result of the sensor for calibration $4_{REF}$.

In addition, the particulate matter detection sensor 4 having the greatest dead mass $Q_0$ among samples extracted from a manufacturing lot can be used as the sensor for calibration $4_{REF}$. In this instance, output is brought closer to the output of the sensor for calibration $4_{REF}$ such as to reduce the sensitivity of particulate matter detection sensors 4 having a small dead mass $Q_0$. Therefore, output variations within manufacturing lots can be very easily reduced.

As a result of correction being made using the correction method of the present invention, the individual differences among particulate matter detection sensors 4 that inevitably arise during the manufacturing process can be reduced.

According to the above-described first embodiment, a method is described in which the sensor output is corrected with the dead mass $Q_0$ as reference. However, the method is not limited thereto. Correction can also be made using the change (gradient) in sensor output in relation to the change in the known amount of particulate matter as reference.

In addition, according to the first embodiment, a configuration is described in which the difference between the output result of the sensor for calibration $4_{REF}$ and the output result of the particulate matter detection sensor 4 to be corrected is measured in advance. The difference is then stored in a memory or the like as correction information and used to adjust each applied voltage $V_{OUT}$. However, the configuration is not limited thereto. A volume resistor VR that adjusts the output of the applied voltage $V_{OUT}$ may be provided in the booster circuit 500, and adjustment may be made for each apparatus for detecting particulate matter 6.

Moreover, a learning function may be provided in which, under a condition in which the amount of particulate matter within the gas to be measured is stabilized, the output result of the particulate matter detection sensor 4 (such as the rate of increase in sense resistance $R_{SEN}$ per unit time under the same condition) is learned. The applied voltage $V_{OUT}$ is adjusted in relation to degradation over time of the particulate matter detection sensor 4, and correction is made such that the output result is constant in relation to the same condition.

Here, effects on the change in sensor output in relation to the change in the applied voltage $V_{OUT}$ of the particulate matter detection sensor 4 of the present invention, and a method of deciding the lower threshold applied voltage $V_{LL}$ and the upper threshold applied voltage $V_{HL}$ will be described with reference to FIG. 3A and FIG. 3B.

Figure 3A:
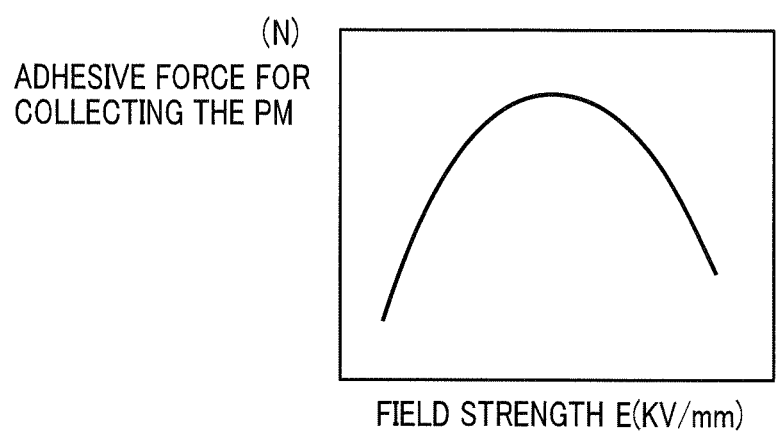
FIG. 3A is a characteristics diagram showing a relationship between the field strength and the collecting performance, the field strength being generated by the voltage applied between the sensing electrodes.

FIG. 3A is a characteristics diagram showing the change in collection performance in relation to the change in voltage per unit distance of the applied voltage $V_{OUT}$ between the sensing electrodes 11 and 12 that opposing each other with a certain amount of space therebetween or, in other words, the change in field strength E (kV/mm), when the distance between the sensing electrodes 11 and 12 of the sensor element 1 used in the present invention is set to, for example, 50 μm.

As shown in FIG. 3A, the relationship between the field strength E and collection performance forms a substantially quadratic curved shape that projects upwards and has a maximum value. An adhesive force F (N) for collecting the particulate matter in the detecting element 13 has been found to gradually increase when the field strength E increases. The adhesive force F (N) has been found to decrease when the field strength E increases beyond a certain extent.

FIG. 3A shows an instance in which the detecting element 13 of the particulate matter detection sensor 4 is disposed in the gas to be measured containing the known amount of particulate matter. The results obtained by measuring the adhesive force F (N) for the particulate matter collected in the detecting element 13 within a certain amount of time while changing the voltage $V_{OUT}$ applied to the sensor element 1 from the power unit 50 are indicated as the collection performance.

Figure 3B:
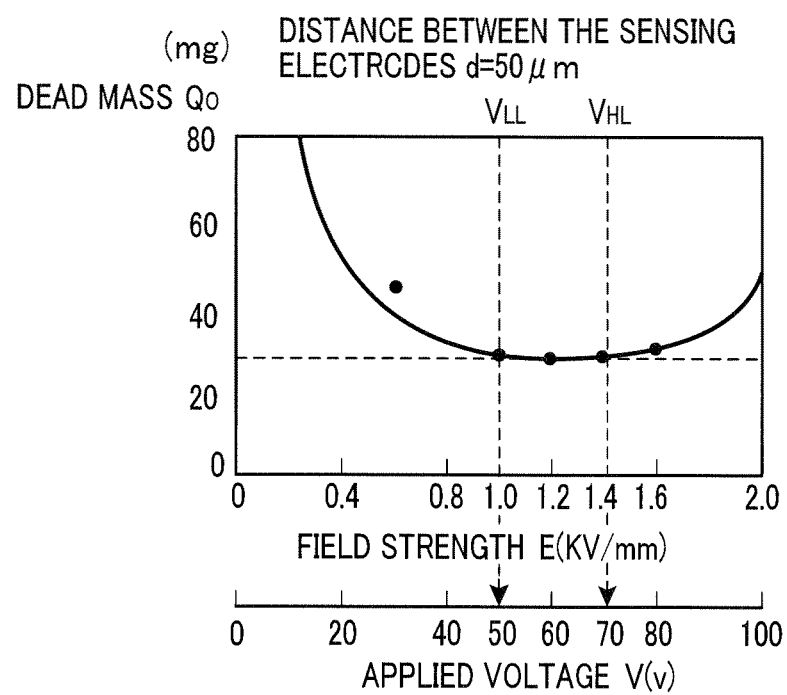
FIG. 3B is a characteristics diagram showing a relationship between field strength and dead mass.

FIG. 3B shows an instance in which the sensing electrodes 11 and 12 are placed opposing each other with an inter-electrode distance of 50 μm. The results obtained by measuring the dead mass $Q_0$ at which the sensor output becomes a certain threshold or more while changing the voltage applied between the sensing electrodes 11 and 12 are shown.

As shown in FIG. 3B, the dead mass $Q_0$ (mg) is changed such as to form a curve where the dead mass $Q_0$ has a minimum in relation to the change in field strength E (kV/mm). The dead mass $Q_0$ can be minimized and held almost constant when the field strength (kV/mm) is within a certain range (1.0 kV/mm to 1.4 kV/mm in the present example). When the field strength E is below 1.0 kV/mm, the dead mass $Q_0$ increases as the field strength E decreases. When the field strength E exceeds 1.4 kv/mm, the dead mass $Q_0$ increases as the field strength E increases.

According to the present example, the inter-electrode distance is set to 50 μm. Therefore, the lower threshold applied voltage $V_{LL}$ can be set to 50V and the upper threshold applied voltage $V_{HL}$ can be set to 70V.

A reason for this is assumed to be that the electrostatic attractive force working on the particulate matter increases as the field strength increases. As a result, collection performance increases. Conversely, when the field strength exceeds a certain amount, the charge built up on the surface of the particulate matter increases. The effect of repulsion among the pieces of particulate matter increases, making collection difficult.

In addition, the range of the field strength E (kV/mm) that maximizes the adhesive force F (N) and the range of the field strength E (kV/mm) that minimizes the dead mass $Q_0$ are found to match.

When the dead mass $Q_0$ during detection of the gas to be measured containing the known amount of particulate matter is less than the dead mass $Q_{0REF}$ of the sensor for calibration $4_{REF}$, the distance between the sensing electrodes 11 and 12 is assumed to be short. Alternatively, the gas to be measured is assumed to be easily guided to the detecting element 13, in regard to the relationship between the sensor element 1 and the cover body 2. In such instances, collection performance can be reduced by the applied voltage $V_{OUT}$ being set to be lower than the lower threshold applied voltage $V_{LL}$ or higher than the upper threshold applied voltage $V_{HL}$. The dead mass $Q_0$ can be brought closer to the dead mass $Q_{0REF}$ for calibration.

On the other hand, the dead mass $Q_0$ during detection of the gas to be measured containing the known amount of particulate matter is equal to or greater than the dead mass $Q_{REF}$ of the sensor for calibration $4_{REF}$, the distance between the sensing electrodes 11 and 12 is assumed to be long. Alternatively, the gas to be measured is assumed to be not easily guided to the detecting element 13, in regard to the relationship between the sensor element 1 and the cover body 2. In such instances, collection performance can be maximized by the applied voltage $V_{OUT}$ being held within the range of the reference voltage, from the lower threshold applied voltage $V_{LL}$ to the upper threshold applied voltage $V_{HL}$. The dead mass $Q_0$ can be prevented from becoming a value further deviating from the dead mass $Q_{0REF}$ for calibration.

At this time, the extent to which the applied voltage $V_{OUT}$ is increased or decreased can be decided by actual measurement in a completion test of the particulate matter detection sensor 4. A memory can be provided in the measuring section 51. The results can be stored in the memory as correction information and fed back to the power unit 50. When an unknown amount of particulate matter actually contained within a gas to be measured is detected, the correction information can be used to decide the applied voltage $V_{OUT}$.

In addition, a configuration is also possible in which the output voltage $V_{OUT}$ is prorated by variable resistance VR and fixed resistance R, and applied to the booster circuit 40. The applied voltage $V_{OUT}$ can be increased and decreased by the variable resistance VR being adjusted based on the dead mass $Q_0$ measured in advance.

Effects according to the first embodiment of the present invention will be described using a comparative example 1, a comparative example 2, and an example 1, with reference to FIG. 4A, FIG. 4B, FIG. 5A, FIG. 5B, FIG. 6A, and FIG. 6B. As the comparative example 1, a conventional particulate matter detection sensor was used that had been completed in a state in which the direction of the sensor element and the direction of the holes in the cover body have been matched during the manufacturing process. As the comparative example 2, a conventional particulate matter detection sensor was used that had been completed by the sensor element and the cover body being assembled in random directions during the manufacturing process, with no regard for the direction of the sensor element and the direction of the holes in the cover body. As the example 1, a particulate matter detection sensor was used that had been completed without regard for the direction of the sensor element and the holes of the cover body during the manufacturing process.

Figure 4A:
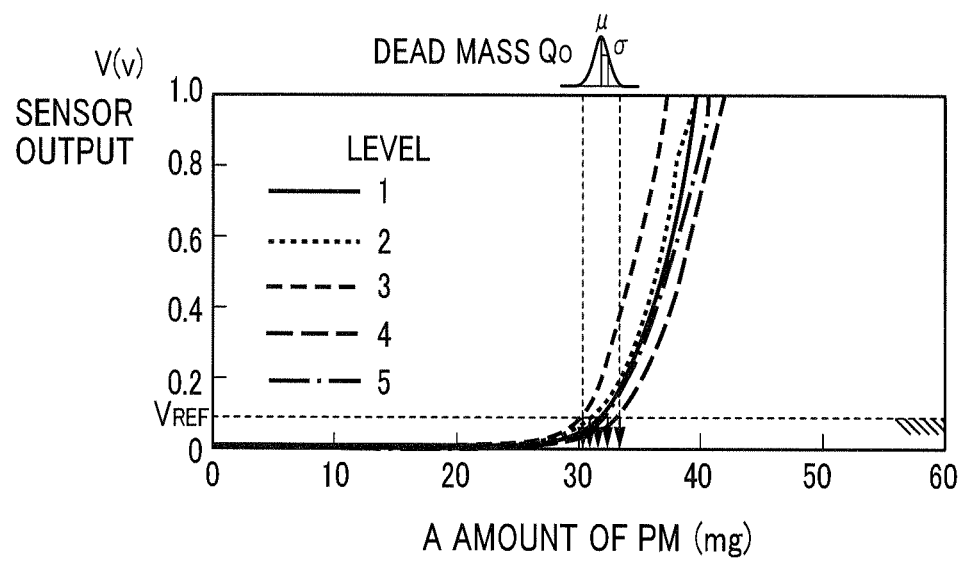
FIG. 4A and FIG. 4B are diagrams showing an individual difference in a state in which the direction of the conventional sensor element and the direction of the cover body have been matched as a comparative example 1.
Figure 4B:
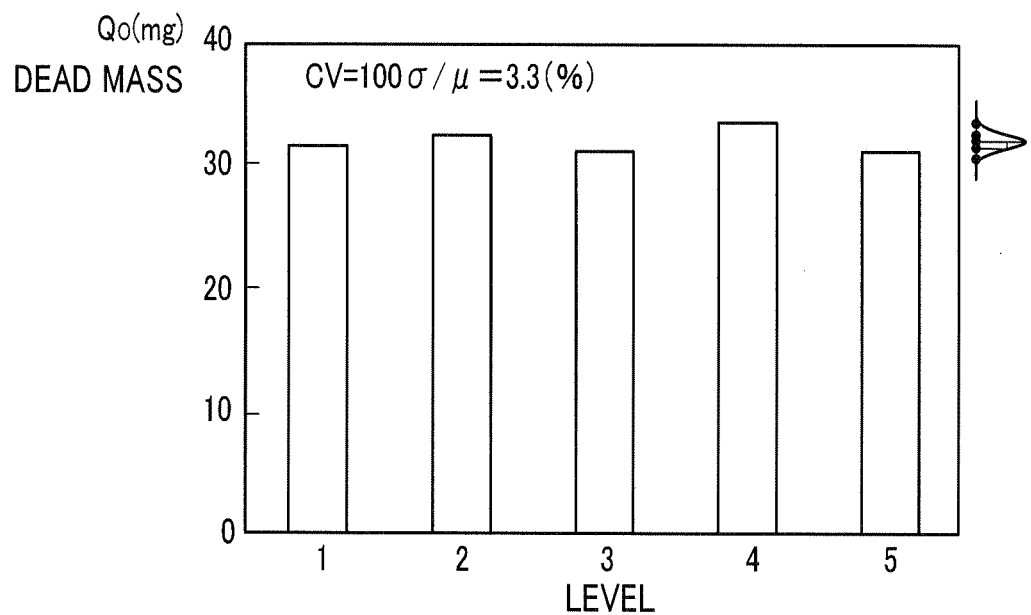

FIG. 4A shows the changes in sensor output when the gas to be measured containing the known amount of particulate matter is measured using a plurality of particulate matter detection sensors of the comparative example 1 (five levels). FIG. 4B shows the results of measurement of the dead mass $Q_0$ until the respective sensor outputs become the predetermined threshold $V_{REF}$ or more.

The threshold $V_{REF}$ is a value at which the output can be detected by the detecting element 13 as an output stable enough to be differentiated from noise. The threshold $V_{REF}$ is set appropriately depending on the sensitivity of the detecting element 13.

Figure 5A:
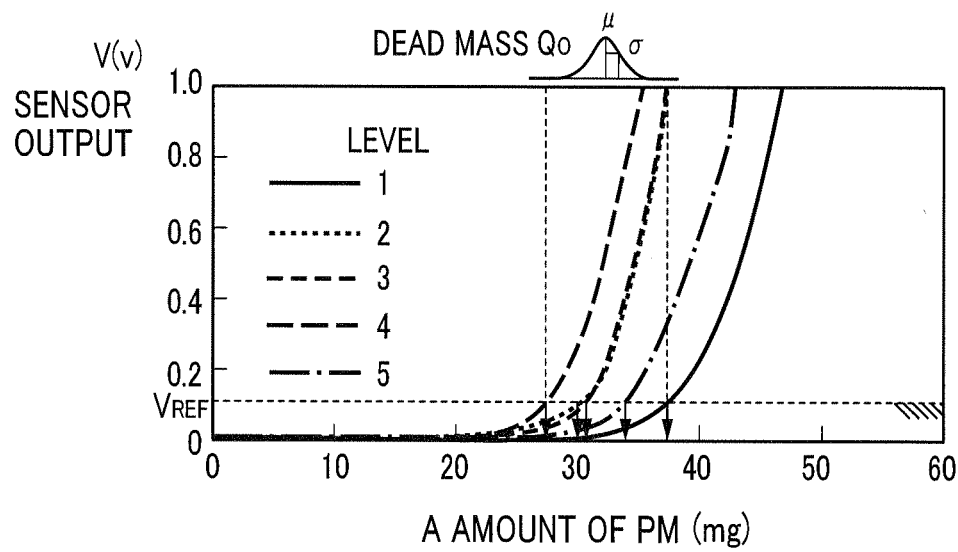
FIG. 5A and FIG. 5B are diagrams showing an individual difference in a state in which the direction of the conventional sensor element and the direction of the cover body have not been matched as a comparative example 2.
Figure 5B:
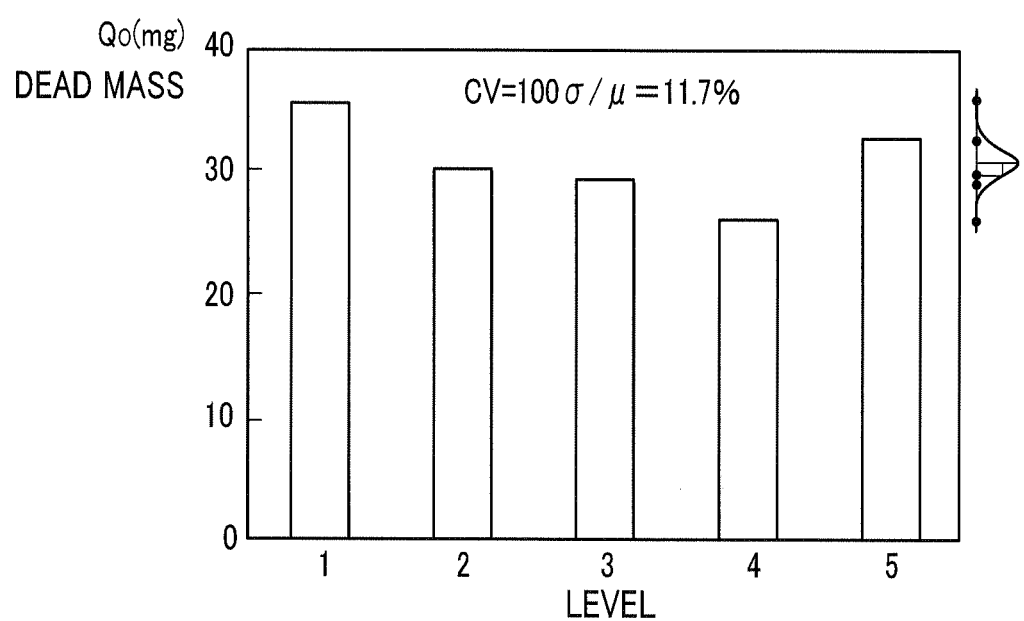

FIG. 5A shows the changes in sensor output when the gas to be measured containing the known amount of particulate matter is measured using a plurality of particulate matter detection sensors of the comparative example 2 (five levels). FIG. 5B shows the results of measurement of the dead mass $Q_0$ until the respective sensor outputs become the predetermined threshold $V_{REF}$ or more.

Figure 6A:
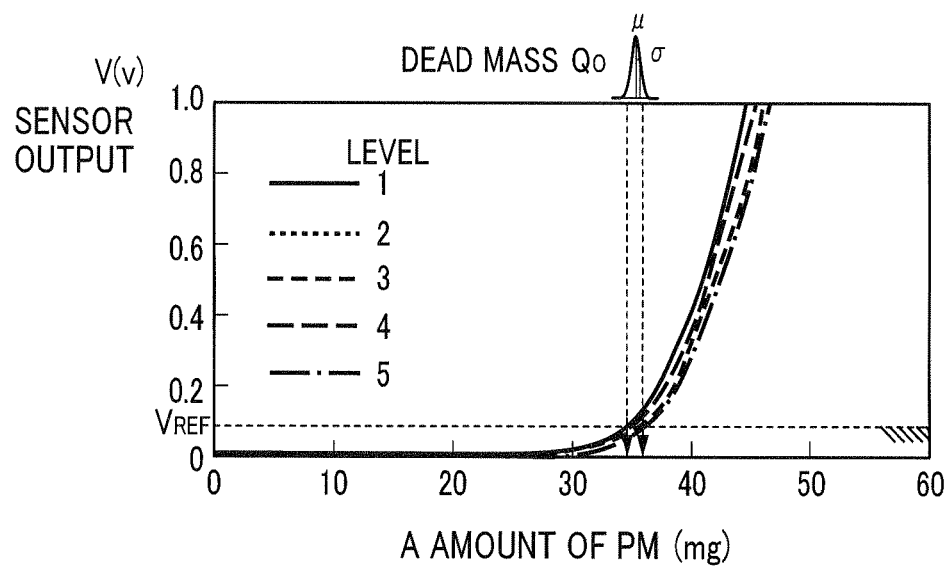
FIG. 6A and FIG. 6B are diagrams showing an individual difference in a state in which the direction of the conventional sensor element and the direction of the cover body have not been matched and sensor output has been corrected by the correction means as an example 1 of the present invention.
Figure 6B:
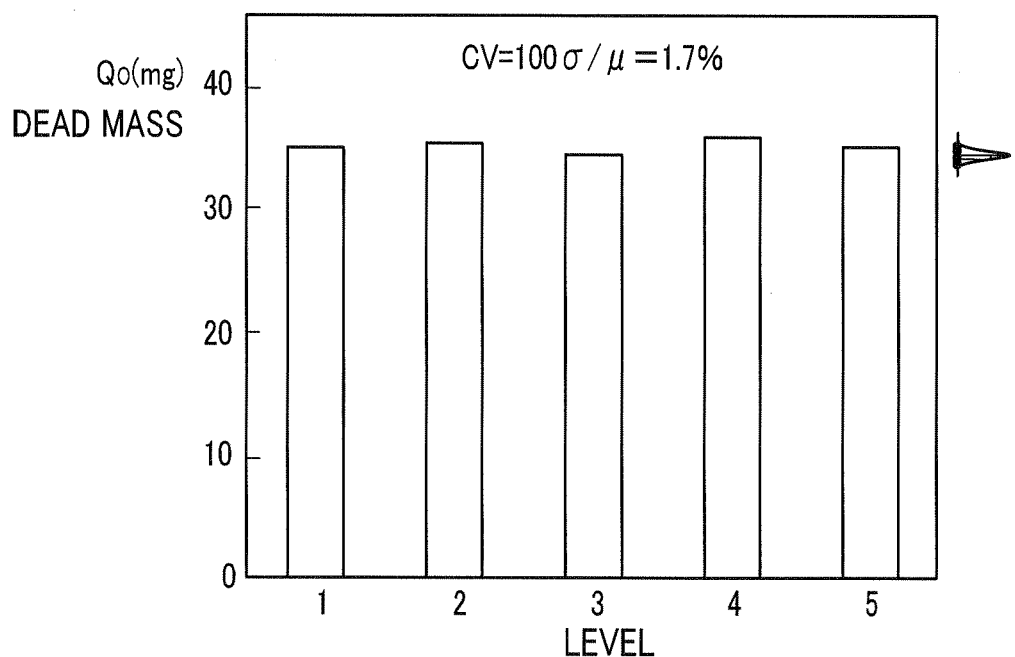

FIG. 6A shows the changes in sensor output when output correction is performed by the correction method of the present invention using a plurality of particulate matter detection sensors of the example 1 of the present invention (five levels). FIG. 6B shows the results of measurement of the dead mass $Q_0$ until the respective sensor outputs become the predetermined threshold $V_{REF}$ or more.

According to the first embodiment, as shown in FIG. 1A, an example of a configuration is described in which the sensing electrodes 11 and 12 are each formed into a comb shape. The sensing electrodes 11 and 12 having mutually differing polarities are disposed such as to be aligned in an alternating manner at a constant interval. The sensing electrodes 11 and 12 detect a resistance value that changes depending on the amount of PM accumulated between the sensing electrodes 11 and 12. However, in the present invention, the shape of the sensing electrodes 11 and 12 is not limited to the comb shape. In addition, the sensing electrodes 11 and 12 are merely required to detect an electrical characteristic that changes depending on the amount of particulate matter accumulated in the detecting element, as the electrical characteristic to be detected. In addition to resistance value, inductance, capacitance, impedance, and the like may be used.

For example, a configuration is possible in which the sensing electrode is formed by a porous electrode. A resistance value that changes depending on the amount of particulate matter accumulated on the surface of the porous electrode may be detected. In addition, a configuration is also possible in which the surface of the sensing electrode is covered by a dielectric layer or an insulating layer. Capacitance that changes depending on the amount of particulate matter accumulated on the surface of the layer may be detected.

Furthermore, a configuration is also possible in which the sensor element 1 includes a heating section that has a heating element that generates heat by being energized. The heating section heats and removes the particulate matter accumulated between the sensing electrodes 11 and 12.

As shown in FIG. 4B, in the particulate matter detection sensor of the comparative example 1, variations with a coefficient of variation CV of 3.3% are found to have occurred in the dead mass $Q_0$.

In the comparative example 1, the sensor element 1 and the cover body 2 are assembled such that the directions match, to eliminate the effects of positional misalignment of the holes in the cover body 2 and the like. Therefore, the variation is considered to have occurred as a result of differences occurring in the amount of particulate matter accumulated until the sensor output becomes a predetermined threshold or more, mainly due to variations in the distance between sensing electrodes.

As shown in FIG. 5B, in the particulate matter detection sensor of the comparative example 2, variations with a coefficient of variation CV of 11.7% are found to have occurred in the dead mass $Q_0$.

In the comparative example 2, assembly is performed with no regard for the directionality of the holes in the cover body. Therefore, the variation is considered to have occurred as a result of differences occurring in the amount of particulate matter guided into the cover body due to positional misalignment of the holes in the cover body, in addition to the variations in the distance between sensing electrodes.

On the other hand, as shown in FIG. 6B, in the example 1, mean value μ is slightly higher compared to that of the comparative example 1. However, standard deviation σ has decreased. The coefficient of variation CV has significantly decreased to 1.7%. Therefore, very highly reliable particulate matter detection can be performed using the apparatus for detecting particulate matter 6 according to the first embodiment of the present invention.

Figure 7A:
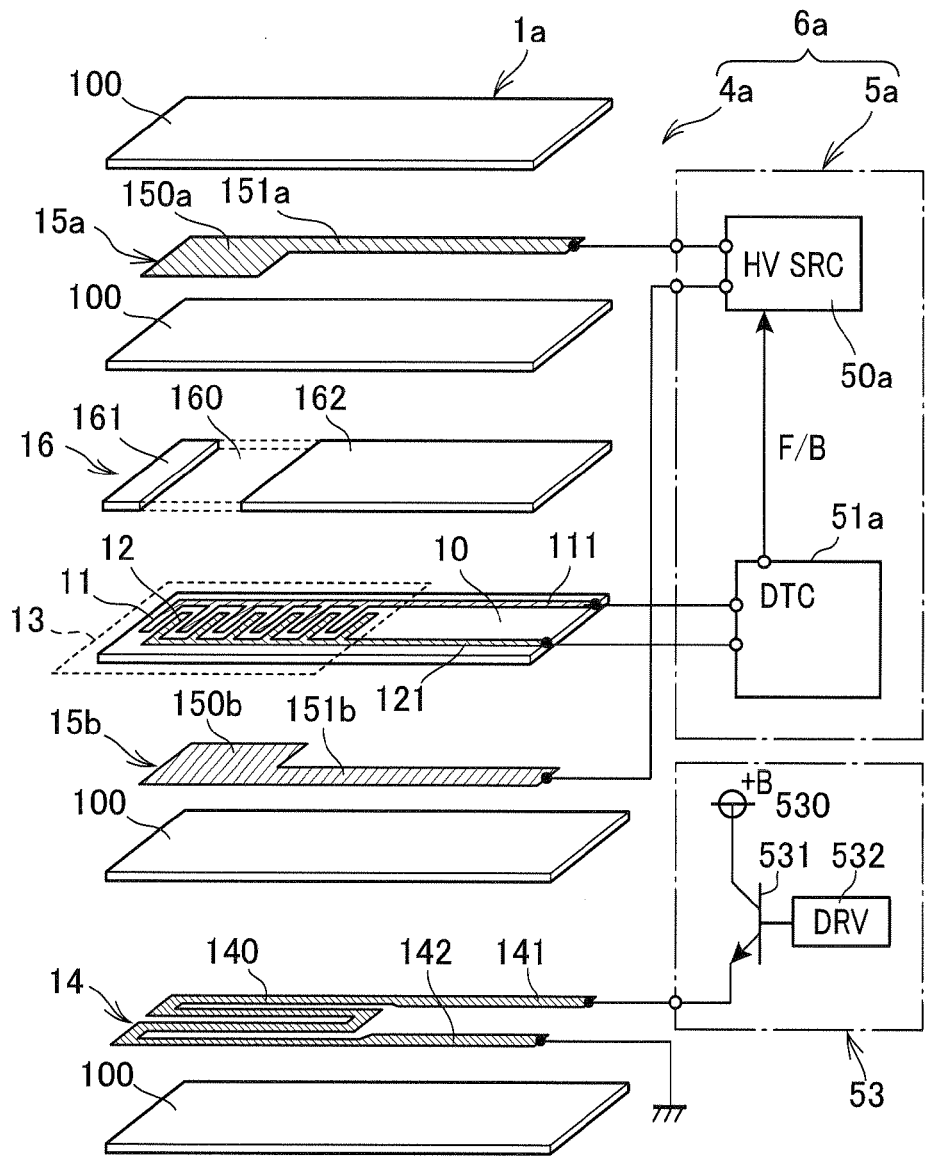
FIG. 7A and FIG. 7B are modification of apparatus for detecting particulate matter according to the first embodiment of the present invention.
Figure 7B:
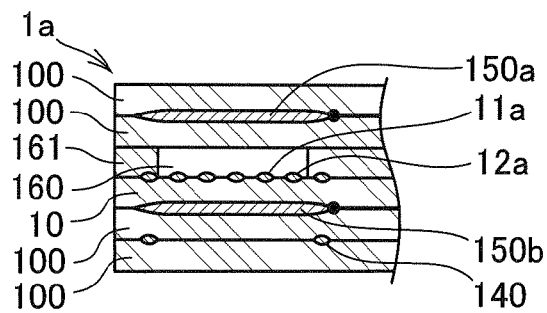

Second Embodiment (FIG. 7A and FIG. 7B)

An apparatus for detecting particulate matter 6a according to a second embodiment of the present invention will be described with reference to FIG. 7A and FIG. 7B. In the descriptions hereafter, configurations that are the same as those according to the first embodiment are given the same reference numbers. Descriptions thereof are omitted. Only characteristic sections are described. The cover body 2 and the housing 3 in the embodiments and comparative examples hereafter are not particularly limited and have the same configuration as those according to the first embodiment.

According to the first embodiment, a configuration is described in which the sensing electrodes 11 and 12 of the sensor element 1 also serve as electrodes for collecting. A high voltage is applied between the sensing electrodes 11 and 12 and the PM is collected in the detecting element 13. The apparatus for detecting particulate matter 6a according to the second embodiment differs in that, in a sensor element 1a according to the second embodiment, a pair of electrodes for collecting 15a and 15b is provided separately from the sensing electrodes 11 and 12. A high voltage is applied between the electrodes for collecting 15a and 15b from a field generation power unit 50a. An electric field is generated within a collecting space 160 provided between the electrodes for collecting 15a and 15b. The PM is collected in a detecting element 13a by electrostatic attractive force.

In a manner similar to that according to the first embodiment, the resistance value that changes depending on the amount of PM accumulated between the sensing electrodes 11 and 12 is detected as the electrical characteristic.

The electrodes for collecting 15a and 15b are disposed opposing each other such as to sandwich the detecting element 13a. Both surfaces of the electrodes for collecting 15a and 15b are sandwiched by the plate-shaped insulating substrate 10 or an insulating substrate 100. The electrodes for collecting 15a and 15b are insulated from each other. The electrode for collecting 15a is composed of a field generating section 150a and a lead portion 151a. The electrode for collecting 15b is composed of a field generating section 150b and a lead portion 151b. The electrodes for collecting 15a and 15b are connected to the field generation power unit 50a.

In addition, the apparatus for detecting particulate matter 6a according to the second embodiment differs in that a collecting space formation layer 16 composed of an insulating substrate is formed such as to cover the detecting element 13. A portion of the detecting element 13 is exposed to the collecting space 160 that is open on both side surfaces.

Furthermore, a heating section 14 is provided that generates heat by being energized. The heating section 14 heats and removes the PM accumulated in the detecting element 13.

The heating section 14 is composed of a heating element 140 and lead portions 141 and 142. The heating element 140 is sandwiched by the insulating substrate 10 and the insulating substrate 100. The heating section 14 is provided such as to be layered onto the detecting element 13. The heating section 14 is connected to a heating element energization control device 53.

In a manner similar to the insulating substrate 10 according to the first embodiment, the insulating substrate 100 is composed of a known ceramic insulating material, such as alumina.

According to the second embodiment as well, in a manner similar to the first embodiment, the applied voltage correction means 511 compares the dead mass $Q_0$ with the dead mass $Q_{0REF}$ of the sensor for calibration 4REF. The dead mass $Q_0$ is that at which the sense resistance RSEN detected by the means for measuring sense resistance 510 using the gas to be measured for calibration containing the known amount of particulate matter is a predetermined threshold or greater than this threshold. The dead mass $Q_{0REF}$ is detected by the external correction means 7 in relation to the gas to be measured for calibration. The applied voltage correction means 511 then increases and decreases the voltage applied by the field generation power unit 50a such that the dead mass $Q_0$ and the dead mass $Q_{0REF}$ of the sensor for calibration $4_{REF}$ match. As a result, effects similar to those according to the first embodiment can be achieved.

In addition, according to the second embodiment, the sensing electrodes 11 and 12 are provided separately from the electrodes for collecting 15a and 15b. The applied voltage for detecting the resistance value and the applied voltage for collecting the PM are set independently. As a result, detection accuracy is further improved.

Moreover, according to the second embodiment, in addition to the effects similar to those according to the first embodiment, the PM is pulled into the collecting space 160 by the attractive force generated by the electrical field generated between the electrodes for collecting 15a and 15b. The collecting space 160 is open towards both side-surface directions at the tip end side of the sensor element 1a. Therefore, the effects of differences in flow rate of the gas to be measured within the cover body 2 due to variations in assembly direction of the cover body 1 can be reduced.
Third Embodiment (FIG. 8 to FIG. 11)

An apparatus for detecting particulate matter 6b according to a third embodiment of the present invention will be described with reference to FIG. 8, FIG. 9, FIG. 10, and FIG. 11. The apparatus for detecting particulate matter 6b according to the third embodiment differs in that the amount of PM accumulated in the detecting element is measured using capacitance C. Specifically, sensing electrodes 11b and 12b are covered by the insulating substrate 100. The sensing electrodes 11b and 12b detect capacitance C that changes depending on the amount of PM accumulated in the collecting space 160.

Even when the capacitance C in the detecting element 13 is measured as the electrical characteristic, in a manner similar to those according to the above-described embodiments, the applied voltage from the field generation power unit decided based on comparison of individual differences with the sensor for calibration $4_{REF}$ can be increased and decreased. As a result, effects similar to those according to the above-described embodiments can be achieved.

In addition, according to the second embodiment, an example is described in which the heating section 14 is layered on one side of the detecting element 13a. According to the third embodiment, heating sections 14a and 14b are layered further outside the electrodes for collecting 15a and 15b. The detecting element 13b is heated from both surfaces thereof.

As a result of this configuration, the PM accumulated on the inner peripheral surfaces of the insulating substrates 10, 161, 162, and 100 segmenting the collecting space 160 can be removed with certainty.

Figure 9:
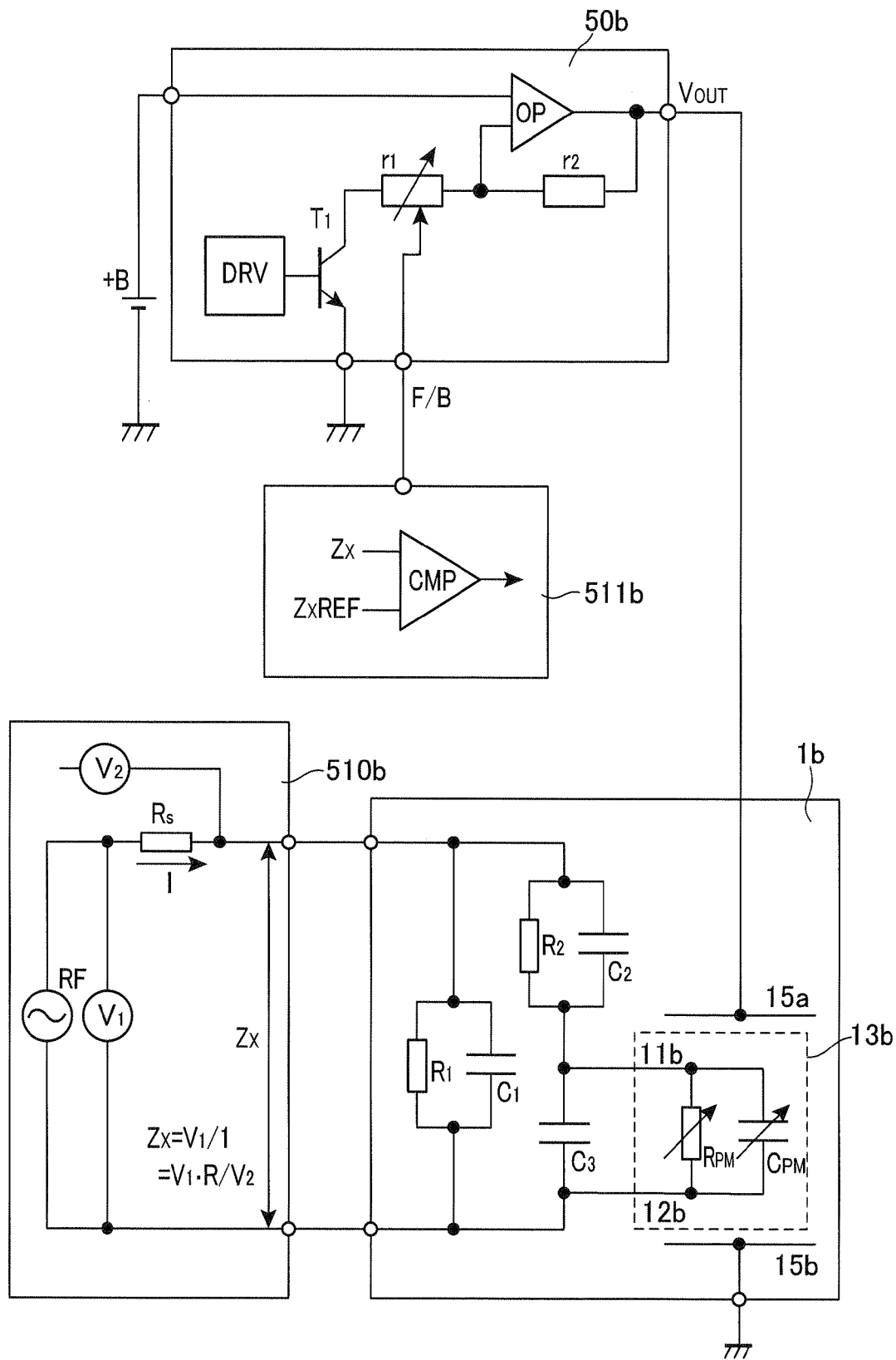
FIG. 9 is a diagram showing an example of a circuit diagram used in the apparatus for detecting particulate matter as shown FIG. 8.

As shown in FIG. 9, a sensor element 1b according to the third embodiment can be expressed by an equivalent circuit in which capacitance $C_{PM}$ and resistance value $R_{PM}$ that change depending on the amount of PM accumulated between the sensing electrodes 11b and 12b, parasitic capacitances $C_1$ and $C_2$ that are parasitic on the lead portions 111b and 121b, and internal resistances $R_1$ and $R_2$ are connected. An impedance Zx between input terminals of an electrical characteristic measuring section 510b can be detected by a known impedance measuring method, such as the so-called I-V method.

Specifically, using voltage $V_1$ applied from an oscillator RF having predetermined frequency characteristics and potential difference $V_2$ detected between both ends of a known resistance value $R_S$, the impedance $Z_X$ is calculated by $Z_X = V_1/I = (V_1/V_2) \cdot R_S$.

Figure 8:
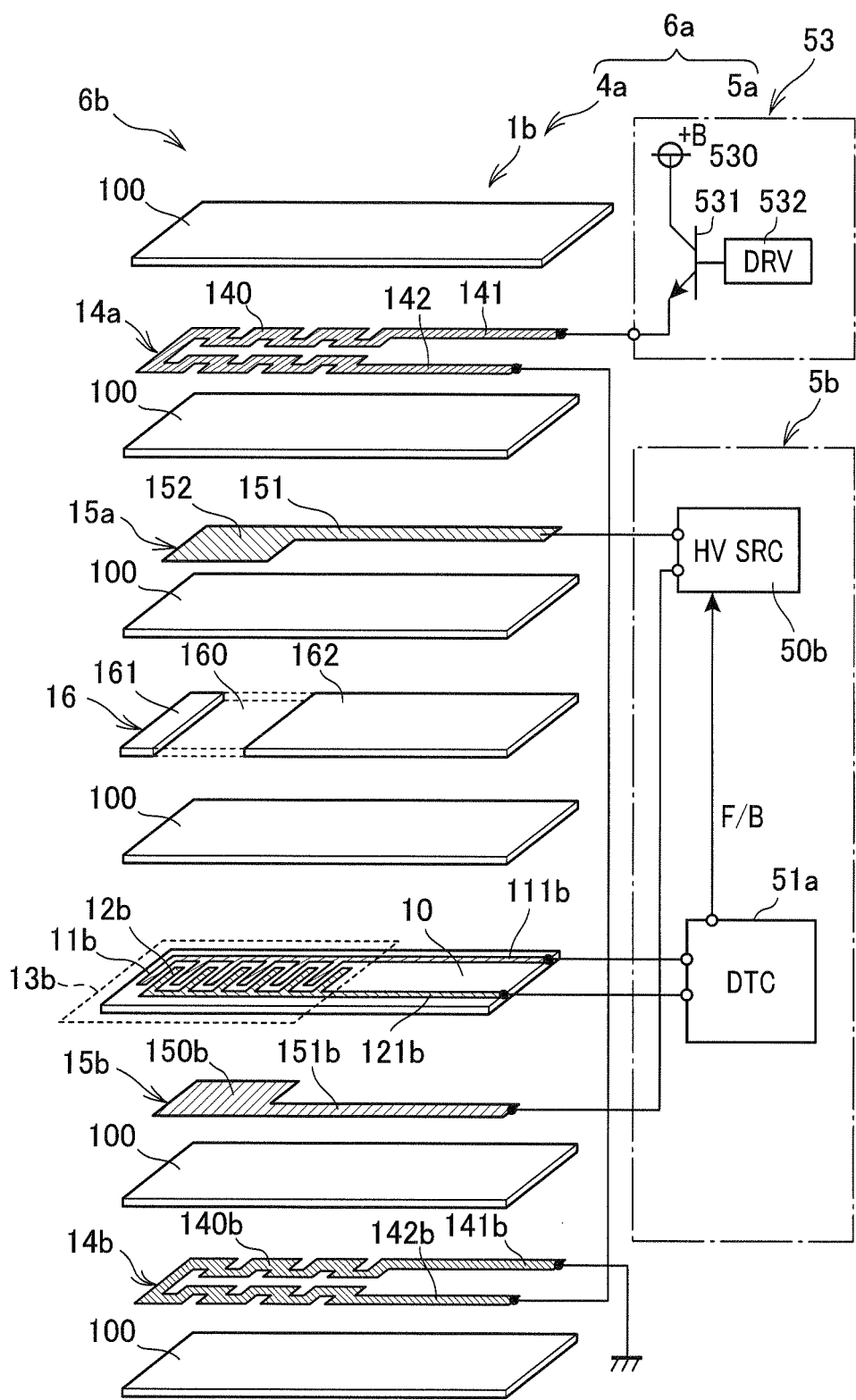
FIG. 8 is a deployment perspective view of apparatus for detecting particulate matter according to the second embodiment of the present invention.

Furthermore, according to the third embodiment, detected impedance $Z_{XREF}$ and detected impedance $Z_X$ are compared using a sensor for calibration $4b_{REF}$ having a configuration similar to the particulate matter detection sensor 4b in FIG. 8. The detected impedance $Z_{XREF}$ is in relation to gas to be measured for calibration containing the known amount of PM. As a result, the resistance value of a variable resistor $r_1$ is set to increase and decrease the applied voltage $V_{OUT}$ of the field generation power unit 50b. Amplification ratio of an amplifier OP is increased and decreased based on a ratio of the resistance value of the variable resistor $r_1$ to a resistor divider value $r_2$.

As a result of this configuration, the applied voltage $V_{OUT}$ of the field generation power unit 50b can be arbitrarily corrected to bring the output in relation to the gas to be measured for calibration closer to the output of the sensor for calibration $4b_{REF}$.

According to the third embodiment, testing similar to that according to the first embodiment was performed using the apparatus for detecting particulate matter 6b shown in FIG. 8. The apparatus for detecting particulate matter 6b for which the correction method of the present invention was not used is a comparative example 3. The apparatus for detecting particulate matter 6b to which the correction method of the present invention was applied is an example 2.

Figure 10A:
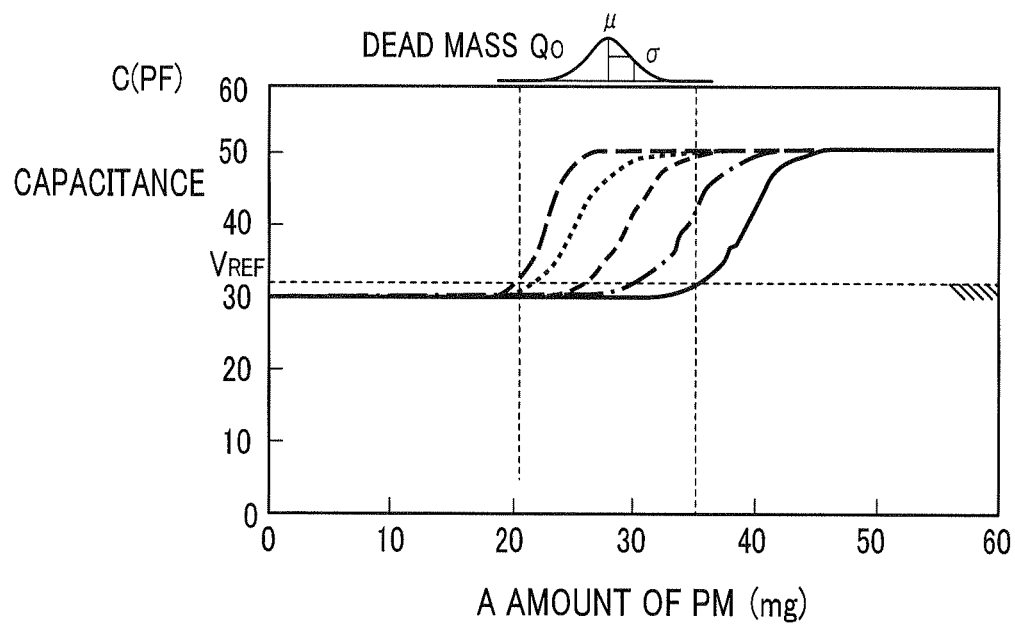
FIG. 10A and FIG. 10B are characteristic diagrams showing the problem in a state in which the apparatus similar to the apparatus as shown as FIG. 8 has not been corrected by using the correction method of the present invention as a comparative example 3.
Figure 10B:
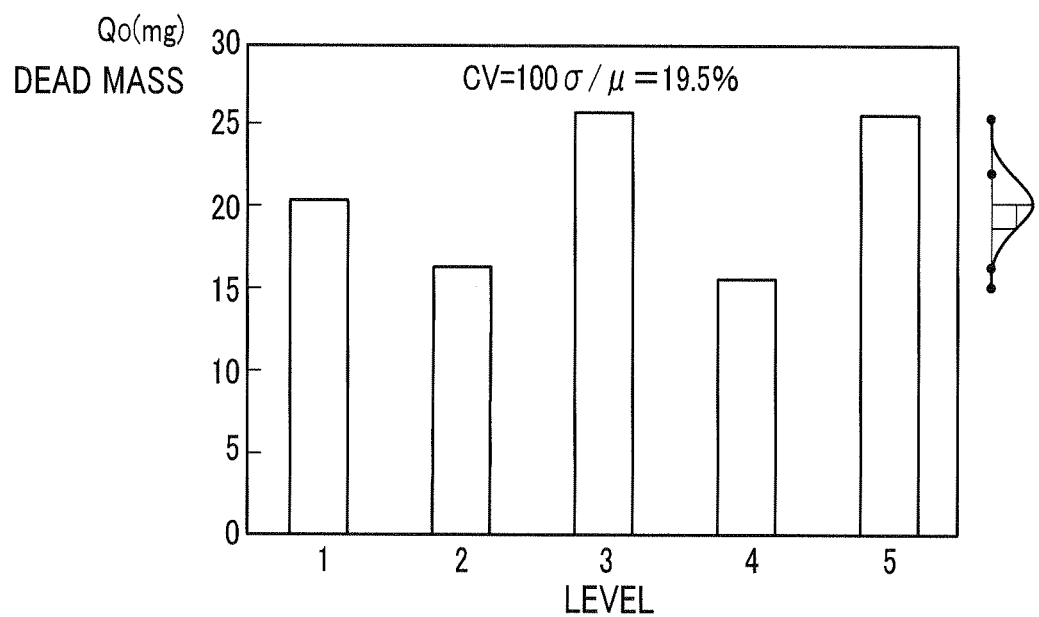

As shown in FIG. 10B, even when the amount of PM is detected using the capacitance (impedance $Z_X$), significant variations (coefficient of variation CV of 19.5%) are clearly seen in the dead mass $Q_O$ when the correction method of the present invention is not used.

Figure 11A:
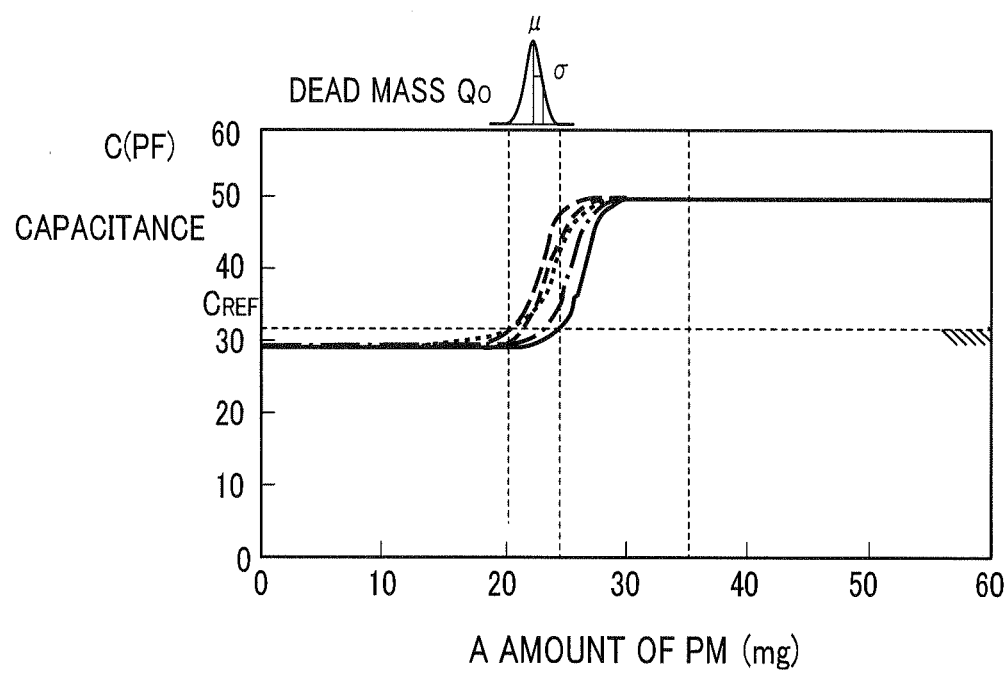
Figure 11B:
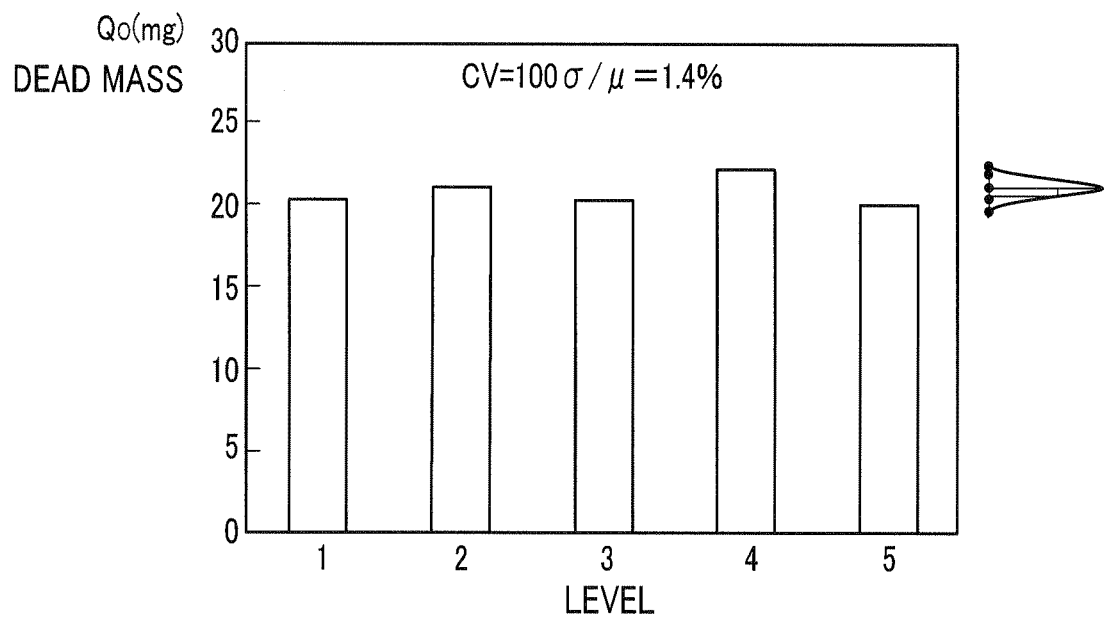

On the other hand, as shown in FIG. 11B, the variations in dead mass $Q_O$ are clearly reduced (coefficient of variation CV of 1.4%) in the example 2.

Therefore, very highly reliable particulate matter detection can be performed using the apparatus for detecting particulate matter according to the third embodiment of the present invention configured to measure the amount of PM accumulated in the detecting element using capacitance.

Fourth Embodiment (FIG. 12)

An apparatus for detecting particulate matter according to a fourth embodiment will be described with reference to FIG. 12.

In the apparatus for detecting particulate matter $6b$ shown in FIG. 8, the sensing electrodes $11b$ and $12b$ are provided separately from the electrodes for collecting $15a$ and $15b$. However, in an apparatus for detecting particulate matter $6c$ according to the fourth embodiment, the sensing electrodes $11c$ and $12c$ are used as the electrodes for collecting.

As shown in FIG. 12, the sensing electrode $11b$ is composed of a sensing electrode plate unit $110c$ and a lead section $111c$. The sensing electrode $12b$ is composed of a sensing electrode plate unit $120c$ and a lead section $121c$. The sensing electrode plate units $110c$ and $120c$ spread in a plate shape. The surfaces of the sensing electrodes $11c$ and $12c$ are respectively covered by plate-shaped insulating substrates $101c$ and $100c$.

As a result of this configuration, a parallel plate for the capacitance C is configured that is proportional to the area of the sensing electrode plate units $110c$ and $120c$ and inversely proportional to the distance between the mutually opposing sensing electrode plate units $110c$ and $120c$. In accompaniment with the change in the amount of collected PM, dielectric constant between the sensing electrode plate units $110c$ and $120c$ change. The capacitance C between the sensing electrodes $11c$ and $12c$ also inevitably changes. As a result of the capacitance C being detected, the amount of PM collected in the collecting space 160 can be calculated.

According to the fourth embodiment, in a manner similar to the above-described embodiments, the applied voltage correcting means 511 compares the dead mass $Q_O$ with the dead mass $Q_{OREF}$ of the sensor for calibration $4_{REF}$. The dead mass $Q_O$ is that at which the sense resistance $R_{SEN}$ detected by the means for measuring sense resistance 510 using the gas to be measured for calibration containing the known amount of particulate matter is a predetermined threshold or greater than this threshold. The dead mass $Q_{OREF}$ is detected by the external correction means 7 in relation to the gas to be measured for calibration. The applied voltage correction means 511 then increases and decreases the voltage applied by the field generation power unit $50a$ such that the dead mass $Q_O$ and the dead mass $Q_{OREF}$ of the sensor for calibration $4_{REF}$ match. Therefore, very highly reliable particulate matter detection can be performed using the apparatus for detecting particulate matter according to the fourth embodiment, even when, for example, the areas of the sensing electrode plate units $110c$ and $120c$ and the inter-electrode distance vary.

Figure 13:
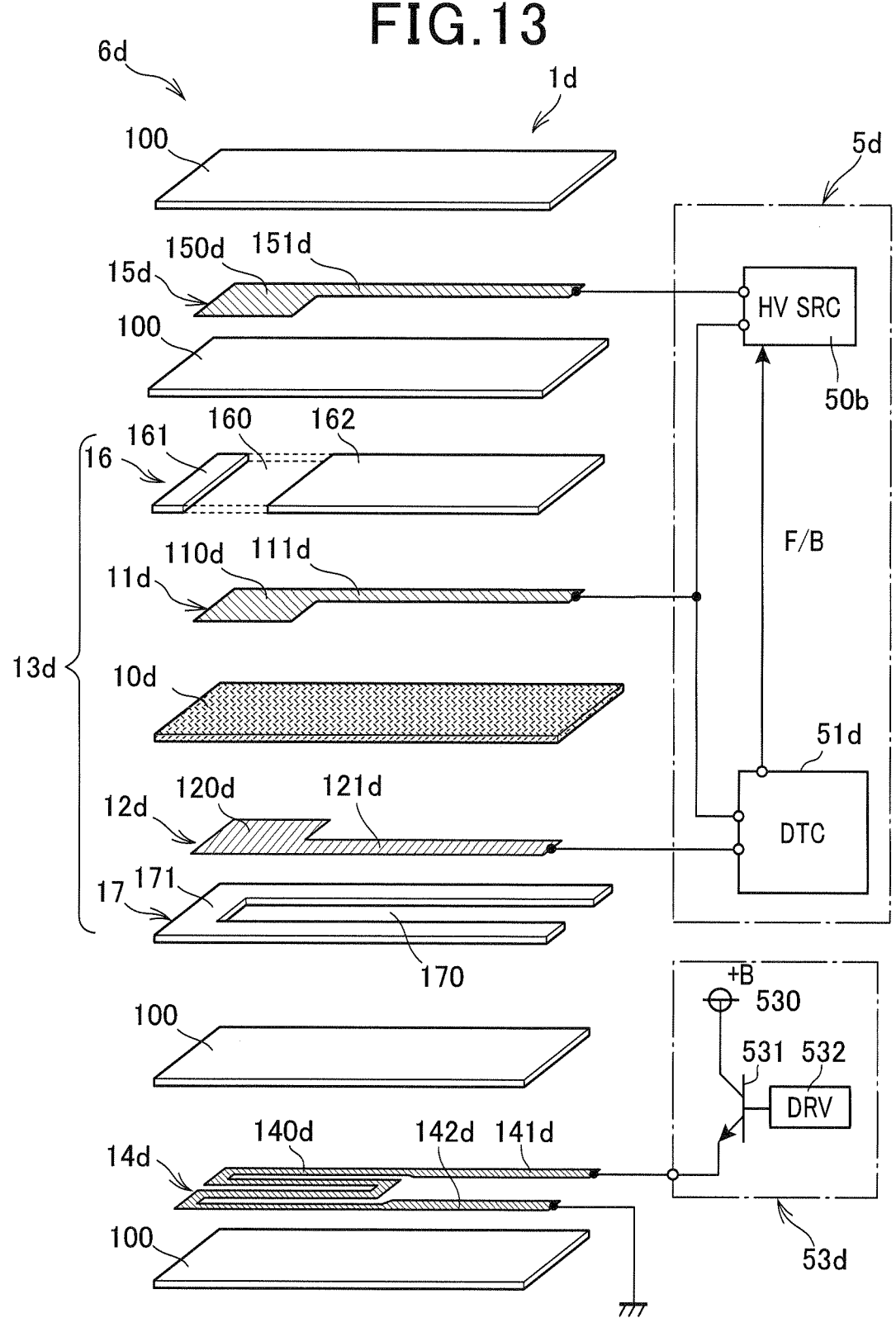
FIG. 13 is a deployment perspective view showing an apparatus for detecting particulate matter according to the third embodiment of the present invention.
Figure 14:
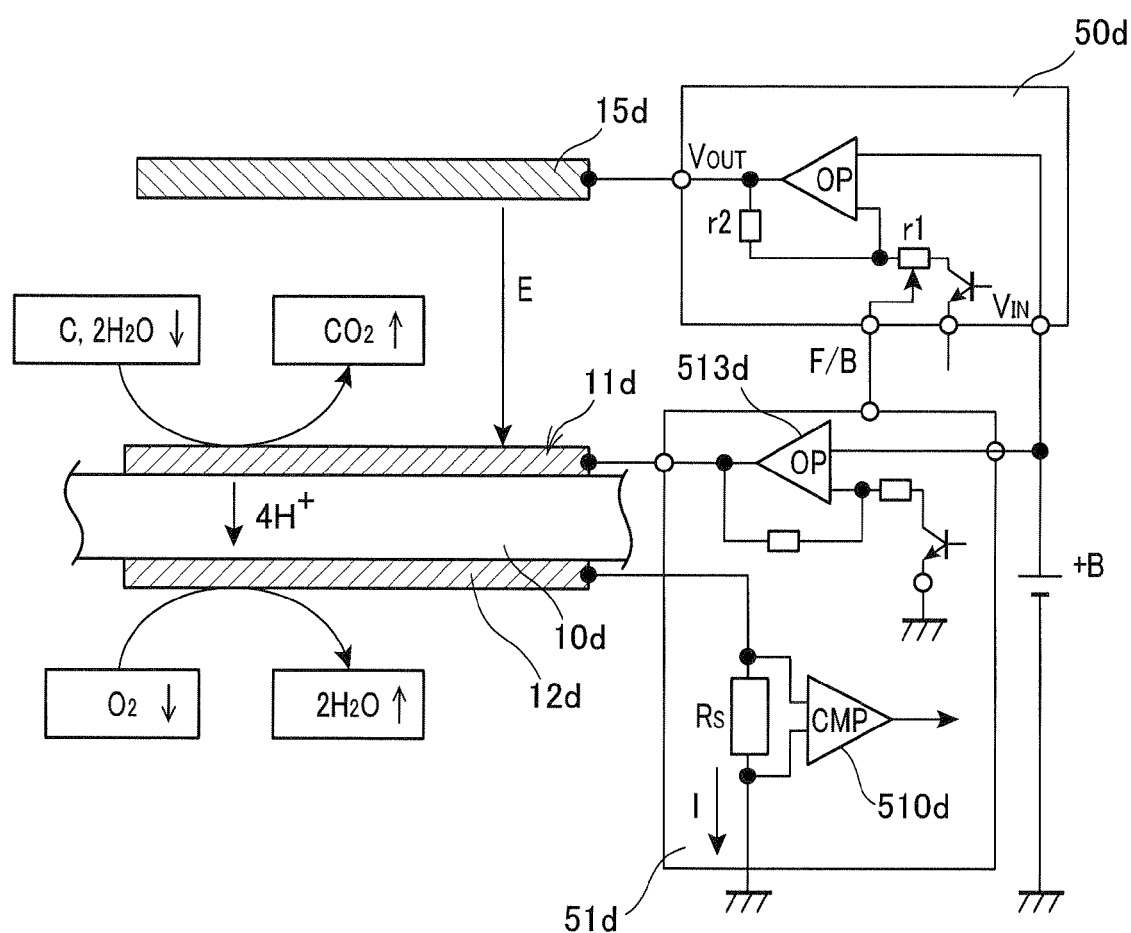
FIG. 14 is a diagram showing an example of a circuit diagram used in the apparatus for detecting particulate matter as shown FIG. 13.

Fifth Embodiment (FIG. 13-FIG. 14)

An apparatus for detecting particulate matter according to the fifth embodiment of the present invention will hereinafter be described with reference to the FIG. 13 and FIG. 14.

An apparatus for detecting particulate matter $6d$ according to the fifth embodiment of the present invention is configured such that PM accumulated in the detecting element $13d$ is removed by oxidation using the electrochemical reaction, and then current flowing at this time is detected in the detecting element $13d$.

In the present embodiment, the sensing electrodes $11d$ and $12d$ are formed by porous electrodes. The sensing electrode $11d$ is composed of plate-shaped sensing electrode plate part $110d$ and lead part $111d$. The sensing electrode $12d$ is composed of plate-shaped sensing electrode plate part $120d$ and lead part $121d$. The sensing electrodes $11d$ and $12d$ are disposed on a surface of a plate-shaped solid electric field layer $10d$ such as to oppose each other. The sensing electrode plate part $110d$ is disposed to oppose the collecting space 160. The sensing electrode plate part $120d$ is disposed to oppose the exhaust space 170 of an exhaust layer 17.

The sensing electrodes $11d$, $12d$ are made of solid electrolyte material which has conductivity caused by a specific ion such as oxygen ion, proton and the like.

As the specific solid electrolyte material, known solid electrolyte materials are used. The known solid electrolyte materials include yttria-stabilized zirconia that has oxygen ion conductivity, and $MP_2O_7$-type pyrophosphate that has proton conductivity and whose part is replaced by a transition metal and the like.

The exhaust space 170 is composed of an insulating material such as alumina and the like. The exhaust space 170 is divided into the substantially U-shaped exhaust space forming layer 171 and the plate-shaped insulator 100.

The heating section $14d$ is provided such as to be layered onto the exhaust layer 17. The heating section $14d$ is covered with the insulator 100 and composed of a heating element $140d$ and lead portions $141d$ and $142d$.

According to the previously described second embodiment, the heating section $14d$ is provided to burn and remove the PM accumulated in the detecting element 13. According to the present embodiment, the PM is removed by oxidation using electrochemical reaction in detecting an amount of PM. The heating section $14d$ is used to heat and activate the solid electric field layer $10d$.

As shown in FIG. 14, a high voltage is applied between the sensing electrodes $11d$ formed on a surface of the solid electric field layer $10d$ and the electrode for collecting $15d$ from a field generation power unit $50d$, and then an electric field is generated. The PM is collected on a surface of the sensing electrode $11d$ by attractive force of the electric field.

Furthermore, voltage is applied between the sensing electrodes $11d$, $12d$ from the power unit for the electrochemical reaction $513d$, and the PM accumulated on a surface of the sensing electrode $11d$ is removed by oxidation using electrochemical reaction. Protons H+ generated by the electrochemical reaction or potential difference generated at both ends of the sense resistor Rs when an electron moves through the solid electric field layer $10d$ is measured by the electrical characteristics measuring section $510d$, and an amount of PM can be calculated.

According to the fifth embodiment, test similar to that according to the first embodiment was performed using the apparatus for detecting particulate matter $6b$ shown in FIG. 12. The apparatus for detecting particulate matter $6b$ for which the correction method of the present invention was not used is a comparative example 4. The apparatus for detecting particulate matter $6b$ to which the correction method of the present invention was applied is an example 3.

Figure 15A:
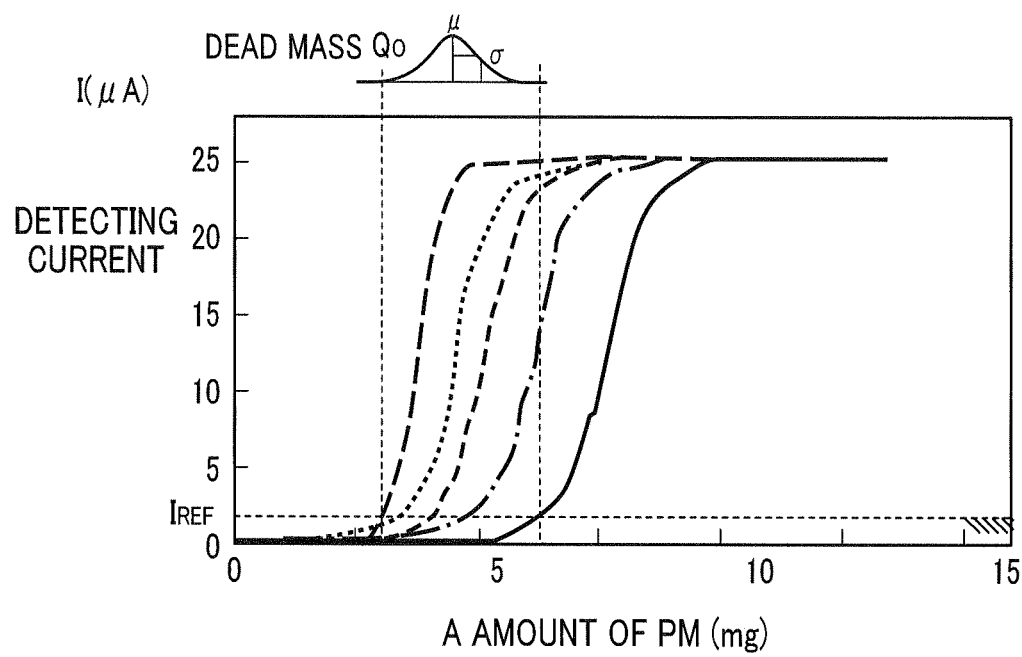
FIG. 15A and FIG. 15B are characteristic diagrams showing the problem in a state in which the apparatus similar to the apparatus as shown as FIG. 13 has not been corrected by using the correcting method of the present invention as a comparative example 4.
Figure 15B:
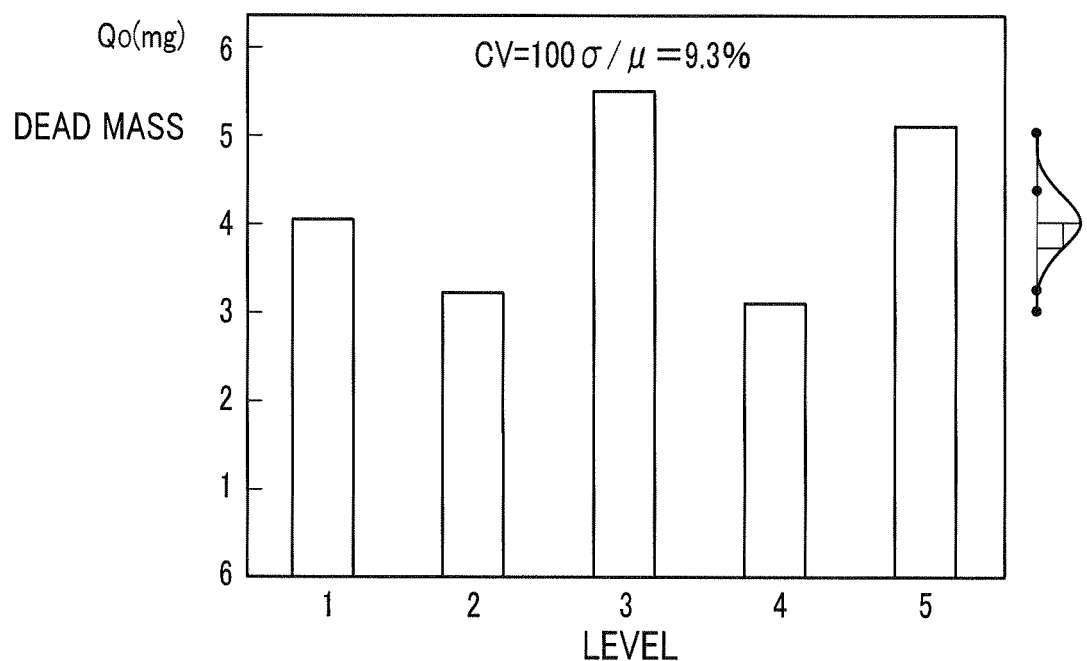

As shown in FIG. 15, even when an amount of PM is detected by the electric current flowing in removing the PM by oxidation using the electrochemical reaction, significant variations (coefficient of variation CV of 9.3%) are clearly seen in the dead mass $Q_0$ when the correction method of the present invention is not used.

Figure 16A:
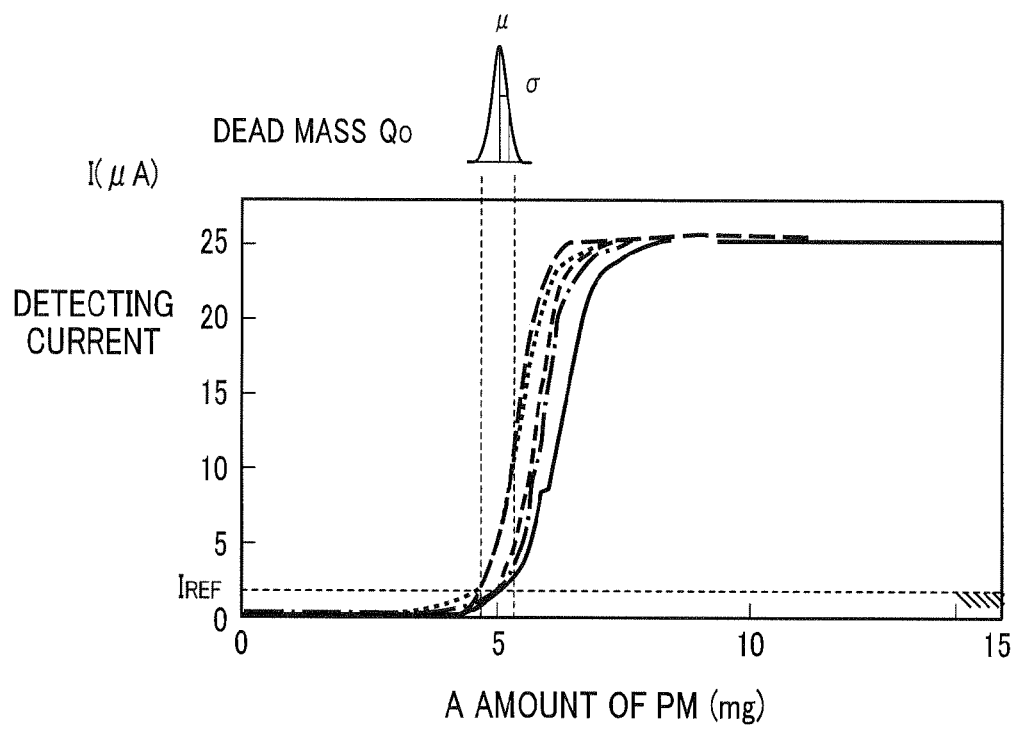
FIG. 16A and FIG. 16B are diagrams showing the effect of the apparatus as shown FIG. 13 as an example 3 of the present invention.
Figure 16B:
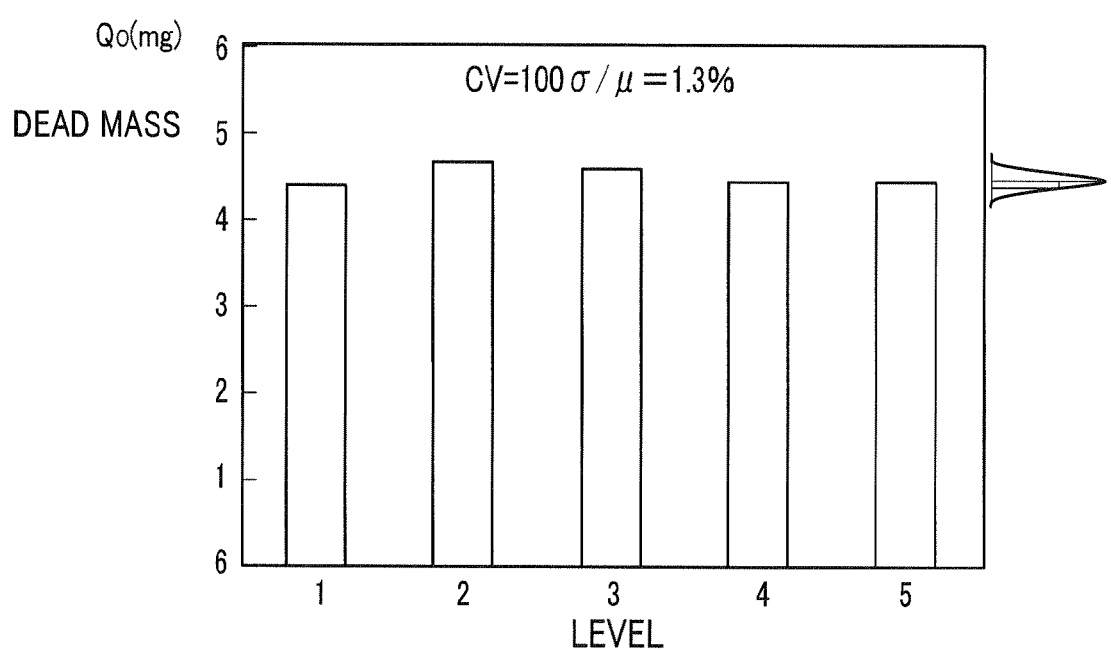

On the other hand, as shown in FIG. 16, as an example 3, when the correction of the field strength is performed using the results compared to the dead mass $Q_{0REF}$ of the sensor calibration $4d_{REF}$ in advance, slight variations (coefficient of variance CV=1.3%) are clearly seen in the dead mass $Q_0$.

Moreover, in the comparative examples 1 to 4 and the examples 1 to 3, mean value μ and standard deviation σ about the dead mass $Q_0$ of multiple sensors for detecting particulate matter are solved, and the coefficient of variance CV is calculated as an indicator of individual differences. The coefficient of variance CV is a value which the standard deviation σ is divided by the mean value μ.

Figure 17:
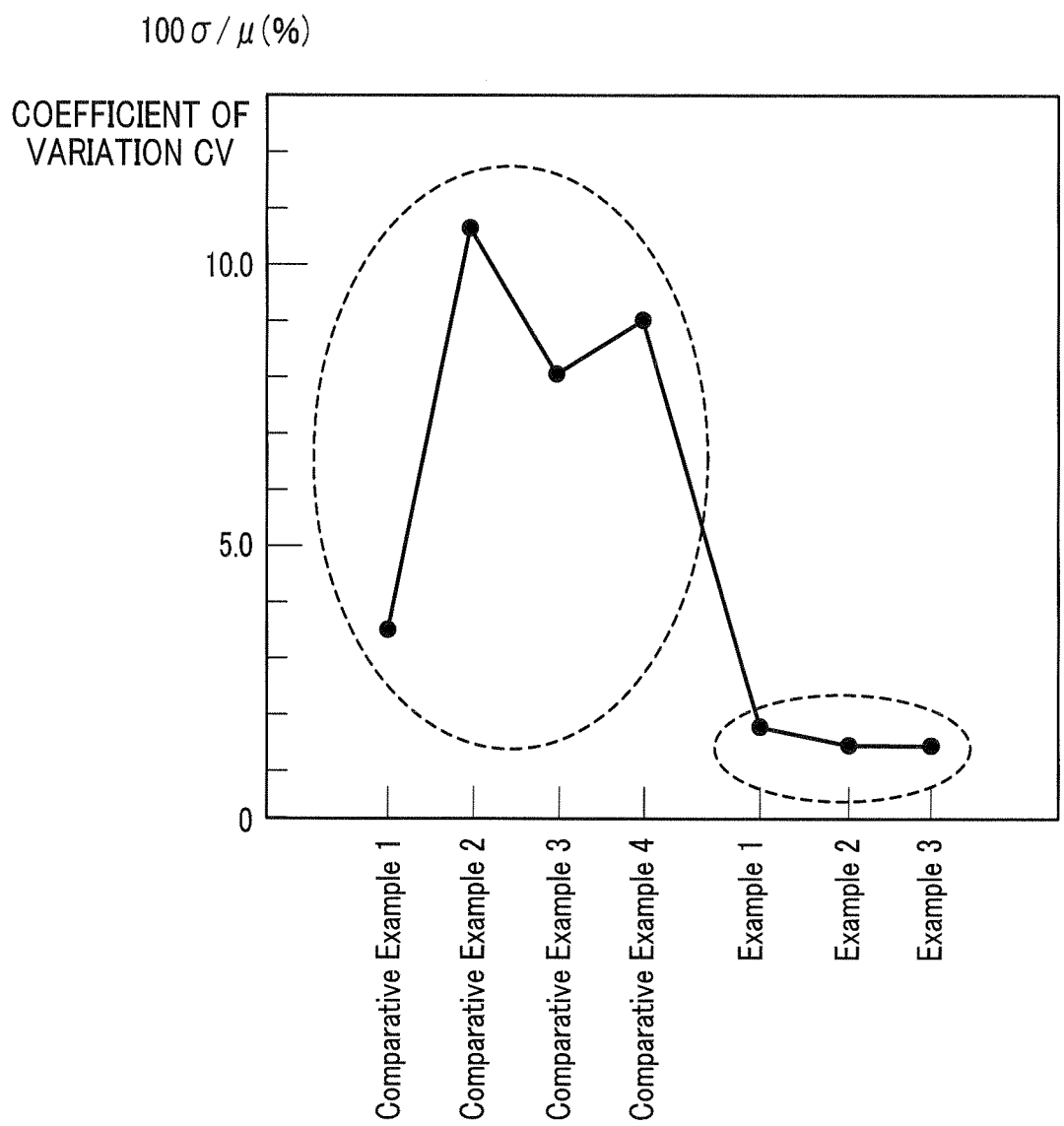
FIG. 17 is a characteristics diagram showing the effect suppressing variations of the sensor output according to the present invention together with comparative examples.

FIG. 17 is a diagram graphed the calculated coefficient of variation in the examples 1 to 3 and comparative examples 1 to 4. As shown in FIG. 17, slight variations are clearly seen in the dead mass in the examples 1 to 3 compared to the comparative examples 1 to 4.

As described above, according to any embodiment of the present invention, the individual differences in sensor output increase in a superimposed manner as a result of variations in inter-electrode distance inevitably occurring during the manufacturing process of the particulate matter detection sensor, and misalignment of the directionality of the sensor elements 1 and 1*a* to 1*d*, and the directionality of the holes provided in the cover body 2. It has been found that, as a result of the voltage applied to the detecting elements of the sensor elements 1 and 1*a* to 1*d* from the field generation power units 50 and 50*a* being corrected depending on individual differences in sensor output, the amount of collected particulate matter can be increased and decreased. As a result, the variations in output results can be reduced.

What is claimed is:

1. An apparatus for detecting particulate matter contained within a gas to be measured, the apparatus comprising:
    a particulate matter detection sensor, including
    a sensor element provided with (i) a collecting electrode so as to form a detecting element, the collecting electrode collecting the particulate matter contained within the gas by using an attractive force generated by an electric field, the collected particulate matter being deposited in the detecting element, and (ii) a sensing electrode outputting a signal showing an electrical characteristic that changes depending on an amount of the particulate matter collected in the detecting element, wherein the collecting electrode is shared by the sensing electrode or the collecting electrode is arranged separately from the sensing electrode,
    a cover body that covers the sensor element for protection; and
    a housing that places the detecting element in the gas to be measured;
    a field generation power unit applying variable voltage to the collecting electrode so as to produce the electric field; and
    a measuring section measuring the electrical characteristic that changes depending on the amount of particulate matter contained within the gas to be measured, the particulate matter being collected and deposited in the detecting element;
    wherein the measuring section comprises
    determining means for determining whether or not a first dead mass is less than a second dead mass, the first dead mass being defined as a dead mass provided until an output of the signal from the sensing electrode in relation to a calibration gas to be measured containing a known amount of the particulate matter becomes a predetermined threshold or more, the second dead mass being a dead mass of a calibration particulate matter detection sensor serving as a reference sensor,
    first collecting means for, when the determining means determines that the first dead mass is equal to or greater than the second dead mass, instructing the field generation power unit to hold the voltage applied to the collecting electrode at a predetermined applied voltage value such that the field strength is corrected to reduce the first dead mass; and
    second collecting means for, when the determining means determines that the first dead mass is less than the second dead mass instructing the field generation power unit to set the voltage applied to the collecting electrode at a value lower than a predetermined lower threshold or higher than a predetermined upper threshold such that the field strength is corrected to increase the first dead mass.

2. The apparatus according to claim 1, wherein the second dead mass is a value measured at an applied voltage in which the field strength becomes 1.0 kV/mm, and the determining means performs the determination based on the measured value.

3. The apparatus according to claim 1, wherein the electrical characteristic is represented by a resistance value or a capacitance that changes depending on the amount of particulate matter contained within the gas to be measured.

4. The apparatus according to claim 1, wherein the electrical characteristic is represented by an electric current flowing during removing the particulate matter by oxidation using an electrochemical reaction.

5. The apparatus according to claim 1, wherein the sensor element includes a heating section that has a heating element generating heat by being energized.

6. A method of correcting voltage applied to a particulate matter detection sensor provided in an apparatus for detecting particulate matter contained within a gas to be measured,
    wherein the particulate matter detection sensor, including
    a sensor element provided with (i) a collecting electrode so as to form a detecting element, the collecting electrode collecting the particulate matter contained within the gas by using an attractive force generated by an electric field, the collected particle particulate matter being deposited in the detecting element, and (ii) a sensing electrode outputting a signal showing an electrical characteristic that changes depending on an amount of the particulate matter collected in the detecting element, wherein the collecting electrode is shared by the sensing electrode or the collecting electrode is arranged separately from the sensing electrode; and
    wherein the apparatus comprises
    a cover body that covers the sensor element for protection;
    a housing that places the detecting element in the gas to be measured;
    a field generation power unit applying variable voltage to the collecting electrode so as to produce the electric field; and
    a measuring section measuring the electrical characteristic that changes depending on the amount of the particulate matter contained within the gas to be measured, the particulate matter being collected and deposited in the detecting element, and
    wherein the method comprising steps of:
    determining whether or not a first dead mass is less than a second dead mass, the first dead mass being defined as a dead mass provided until an output of the signal from the sensing electrode in relation to a calibration gas to be measured containing a known amount of the particulate matter becomes a predetermined threshold or more, the second dead mass being a dead mass of a calibration particulate matter detection sensor serving as a reference sensor;

first instructing, when the first dead mass is equal to or greater than the second dead mass, the field generation power unit to hold the voltage applied to the collecting electrode at a predetermined applied voltage value such that the field strength is corrected to reduce the first dead mass; and second instructing, when the first dead mass is less than to the second dead mass, the field generation power unit to set the voltage applied to the collecting electrode at a value lower than a predetermined lower threshold or higher than a predetermined upper threshold such that the field strength is corrected to increase the first dead mass.

7. The correction method according to claim 6, wherein the second dead mass is a value measured at an applied voltage in which the field strength becomes 1.0 kV/mm, and the determining step performs the determination based on the measured value.

8. The correction method according to claim 6, wherein the calibration particulate matter detection sensor is selected as a sensor from samples extracted from a manufacturing lot thereof, the selected sensor having the greatest second dead mass.

9. The correction method according to claim 6, wherein the electrical characteristic is represented by a resistance value or a capacitance that changes depending on the amount of the particulate matter contained within the gas to be measured.

10. The correction method according to claim 6, wherein the electrical characteristic is represented by an electric current flowing during removing the particulate matter by oxidation using an electrochemical reaction.

11. An apparatus for detecting particulate matter contained within a gas to be measured, the apparatus comprising:

a particulate matter detection sensor, including a sensor element provided with a sensing electrode so as to form a detecting element, the sensing electrode collecting the particulate matter contained within the gas by using an attractive force generated by an electric field, the collected particulate matter being deposited in the detecting element, and the sensing electrode outputting a signal showing an electrical characteristic that changes depending on an amount of the particulate matter collected in the detecting element, a cover body that covers the sensor element for protection; and a housing that places the detecting element in the gas to be measured;

a field generation power unit applying variable voltage to the sensing electrode so as to produce the electric field; and a measuring section measuring the electrical characteristic that changes depending on the amount of particulate matter contained within the gas to be measured, the particulate matter being collected and deposited in the detecting element;

wherein the measuring section comprises determining means for determining whether or not a first dead mass is less than a second dead mass, the first dead mass being defined as a dead mass provided until an output of the signal from the sensing electrode in relation to a calibration gas to be measured containing a known amount of the particulate matter becomes a predetermined threshold or more, the second dead mass being a dead mass of a calibration particulate matter detection sensor serving as a reference sensor, first collecting means for, when the determining means determines that the first dead mass is equal to or greater than the second dead mass, instructing the field generation power unit to hold the voltage applied to the sensing electrode at a predetermined applied voltage value such that the field strength is corrected to reduce the first dead mass; and second collecting means for, when the determining means determines that the first dead mass is less than the second dead mass instructing the field generation power unit to set the voltage applied to the sensing electrode at a value lower than a predetermined lower threshold or higher than a predetermined upper threshold such that the field strength is corrected to increase the first dead mass, wherein the sensing electrode is composed of a pair of electrodes arranged to be opposed to each other with the detecting element provided therebetween, the predetermined lower threshold is a voltage which generates the field strength of 1.0 kV/mm between the sensing electrodes, and the predetermined upper threshold is a voltage which generates the field strength of 1.4 kV/mm between the sensing electrodes.

12. A method of correcting voltage applied to a particulate matter detection sensor provided in an apparatus for detecting particulate matter contained within a gas to be measured, wherein the particulate matter detection sensor, including a sensor element provided with a sensing electrode so as to form a detecting element, the sensing electrode collecting the particulate matter contained within the gas by using an attractive force generated by an electric field, the collected particle particulate matter being deposited in the detecting element, and the sensing electrode outputting a signal showing an electrical characteristic that changes depending on an amount of the particulate matter collected in the detecting element and wherein the apparatus comprises a cover body that covers the sensor element for protection;

a housing that places the detecting element in the gas to be measured;

a field generation power unit applying variable voltage to the sensing electrode so as to produce the electric field; and a measuring section measuring the electrical characteristic that changes depending on the amount of the particulate matter contained within the gas to be measured, the particulate matter being collected and deposited in the detecting element, and wherein the method comprising steps of:

determining whether or not a first dead mass is less than a second dead mass, the first dead mass being defined as a dead mass provided until an output of the signal from the sensing electrode in relation to a calibration gas to be measured containing a known amount of the particulate matter becomes a predetermined threshold or more, the second dead mass being a dead mass of a calibration particulate matter detection sensor serving as a reference sensor;

first instructing, when the first dead mass is equal to or greater than the second dead mass, the field generation power unit to hold the voltage applied to the sensing electrode at a predetermined applied voltage value such that the field strength is corrected to reduce the first dead mass; and second instructing, when the first dead mass is less than to the second dead mass, the field generation power unit to set the voltage applied to the sensing electrode at a value lower than a predetermined lower threshold or higher than a predetermined upper threshold such that the field strength is corrected to increase the first dead mass, wherein the sensing electrode is composed of a pair of electrodes arranged to be opposed to each other with the detecting element provided therebetween, the predetermined lower threshold is a voltage which generates the field strength of 1.0 kV/mm between the sensing electrodes, and the predetermined upper threshold is a voltage which generates the field strength of 1.4 kV/mm between the sensing electrodes.

\* \* \* \* \*